United States Patent
Schlumpberger et al.

(10) Patent No.: US 11,725,200 B2
(45) Date of Patent: Aug. 15, 2023

(54) METHOD FOR ISOLATING RNA WITH HIGH YIELD

(71) Applicant: QIAGEN GmbH, Hilden (DE)

(72) Inventors: Martin Schlumpberger, Hilden (DE); Gabriele Christoffel, Hilden (DE)

(73) Assignee: QIAGEN GMBH, Hilden (DE)

( * ) Notice: Subject to any disclaimer, the term of this patent is extended or adjusted under 35 U.S.C. 154(b) by 494 days.

(21) Appl. No.: 16/650,598

(22) PCT Filed: Sep. 27, 2017

(86) PCT No.: PCT/EP2017/074490
§ 371 (c)(1),
(2) Date: Mar. 25, 2020

(87) PCT Pub. No.: WO2019/063071
PCT Pub. Date: Apr. 4, 2019

(65) Prior Publication Data
US 2021/0102189 A1    Apr. 8, 2021

(51) Int. Cl.
*C12N 15/10* (2006.01)
(52) U.S. Cl.
CPC .............................. *C12N 15/1003* (2013.01)
(58) Field of Classification Search
CPC .............................. C12N 15/1003; C12Q 1/68
See application file for complete search history.

(56) References Cited

U.S. PATENT DOCUMENTS

| | | | | |
|---|---|---|---|---|
| 2007/0185322 | A1* | 8/2007 | Akhavan-Tafti | C12N 15/1006 536/25.4 |
| 2010/0221788 | A1* | 9/2010 | Radmacher | C12N 15/1006 536/25.41 |

FOREIGN PATENT DOCUMENTS

| | | | | |
|---|---|---|---|---|
| CN | 101535501 | A | 9/2009 | |
| WO | 2007098379 | A2 | 8/2007 | |
| WO | 2008/064686 | A1 | 6/2008 | |
| WO | WO-2008064686 | A1 * | 6/2008 | ......... C07K 14/4726 |
| WO | WO-2016009059 | A1 * | 1/2016 | ......... C12N 15/1003 |

OTHER PUBLICATIONS

Kejnovsky et al., "DNA extraction by zinc," Nucleic Acids Res 25(9):1870-1871 (1997).
Kejnovsky et al., "Millimolar concentrations of zinc and other metal cations cause sedimentation of DNA," Nucleic Acids Res 26(23): 5295-5299 (1998).
Tan et al., "DNA, RNA, and Protein Extraction: The Past and the Present," J. Biomedicine and Biotechnol. Article ID 574398, 10 pages (2009).
Zähringer et al., "Old and New Ways to RNA," Lab Times, Feb. 2012:52-60 (2012).
The International Search Report issued in International Application No. PCT/EP2017/074490, dated Dec. 15, 2017.

* cited by examiner

*Primary Examiner* — Narayan K Bhat
(74) *Attorney, Agent, or Firm* — Medler Ferro Woodhouse & Mills PLLC

(57) ABSTRACT

A phenol-free method for isolating a nucleic acid from a sample is provided, said method comprising the following steps: a) adding a precipitation buffer to a sample to prepare an acidic precipitation mixture wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM and precipitating proteins; b) separating the precipitate from the supernatant, wherein the supernatant comprises small RNA having a length of less than 200 nt and large RNA having a length of at least 1000 nt; and c) isolating a nucleic acid from the supernatant. The present method allows to avoid the use of organic solvents during protein precipitation. Also provided is a precipitation buffer.

19 Claims, 4 Drawing Sheets

METHOD FOR ISOLATING RNA WITH HIGH YIELD

Figure 1:
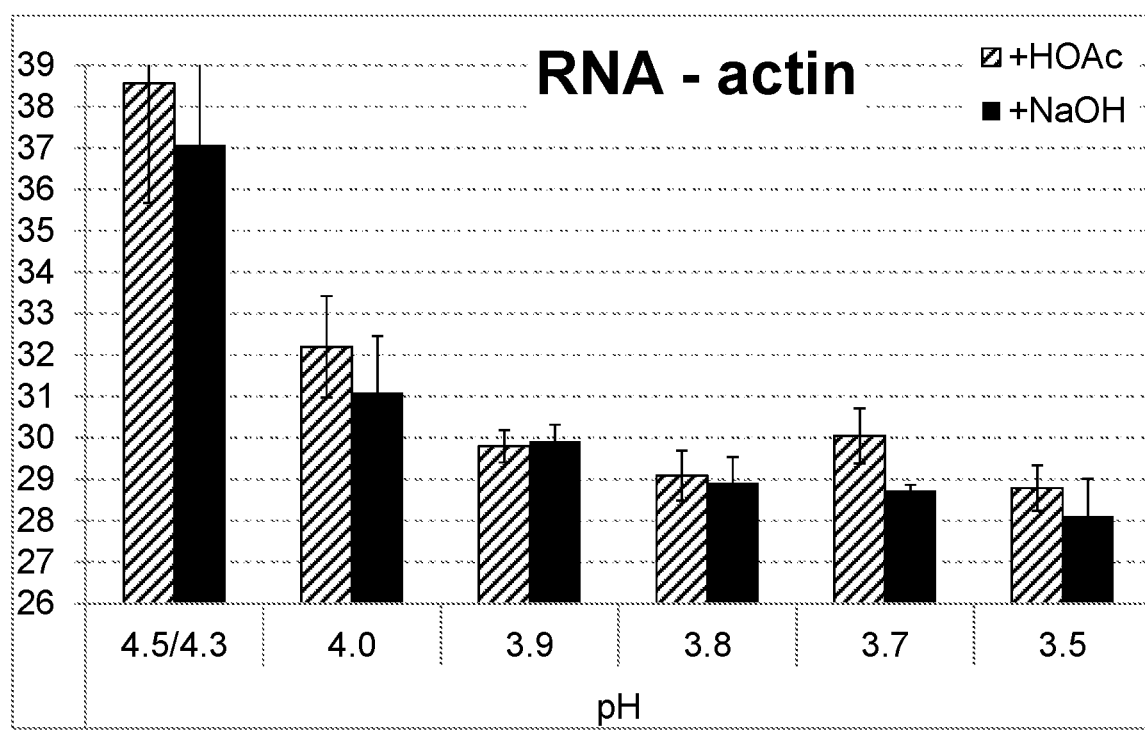

The present invention pertains to a method for isolating a nucleic acid such as RNA from a sample and in particular provides means for efficiently isolating small RNA and large RNA with high yield from various samples, including protein-rich samples by using a phenol-free RNA isolation method.

The study of small nucleic acids in the order of 200 nucleotides or less from various tissues, body fluids and other biological samples is an area of extreme interest and promises to remain one for the future. Small nucleic acids in particular include but are not limited to small RNAs such as inter alia micro RNAs (miRNA) and small interfering RNA molecules both of which can have a powerful effect on the expression of a gene. Furthermore, also other small nuclear and small nucleolar RNAs (e.g. snRNAs and snoRNAs) involved in mRNA and rRNA processing are of interest. Furthermore, nucleic acids such as RNA having a length of 500 nucleotides or less are also often contained as degradation products in other samples and must be efficiently captured therefrom. With the increasing interest in respective small RNAs, the standard isolation procedures have been modified to facilitate the isolation of small nucleic acids and to improve the yield of small nucleic acids. Such improvements were necessary because standard protocols used to isolate total RNA are usually not ideal for isolating small RNAs because small RNA is often not effectively bound using standard methods. Therefore, total RNA isolated using standard procedures usually does not comprise small RNA in sufficient amounts for a subsequent analysis. These low yields are attributable to that small RNAs are either not bound or get lost during the nucleic acid isolation procedure. Therefore, methods were developed that allow the efficient isolation of total RNA, which includes the desired small RNAs or which selectively isolate small RNA (without larger RNA) from the samples.

Common methods designed to isolate small RNA, such as in particular small, single-stranded RNA such as miRNAs, require rather high alcohol concentrations of ≥45% or preferably ≥50% during binding to ensure efficient binding of the small RNA to a nucleic acid binding solid phase. The binding efficiency increases with increasing alcohol concentration. However, these high alcohol concentrations required to ensure efficient RNA binding to the solid phase cause problems which disturb the isolation procedure. In particular when processing protein-rich samples such as plasma, serum or tissue samples, the high alcohol concentration that is required during the RNA binding step can result in that proteins are precipitated onto the solid phase. These precipitates are contaminants that disturb the isolation procedure, because they e.g. bind unspecifically to and thereby block the solid phase and/or are carried over as contaminants into the eluate.

Established methods for isolating small RNA from protein-rich samples therefore include a protein removal step prior to establishing the binding conditions that allow to bind small RNA. Protein removal techniques include e.g. a phenol/chloroform extraction or a protein precipitation step. Other methods employ a time consuming enzymatic protein digestion step such as a digestion with proteinase K. Alternatively, the sample is heavily diluted or the alcohol concentration during binding is reduced which has the drawback that the isolation efficiency is reduced. The problems associated with these known methods are described subsequently in further detail.

Phenol/chloroform-based organic extraction methods are often performed according to the Chomczynski method (Chomczynski and Sacchi, 1987: Single-step method of RNA isolation by acid guanidinium thiocyanate-phenol-chloroform extraction. Anal. Biochem. (162): 156-159). According to said methods, the RNA is concentrated during phenol/chloroform extraction in the aqueous phase and is then subsequently isolated therefrom e.g. by adding alcohol to the aqueous phase and binding the RNA to a nucleic acid binding solid phase. In said RNA binding step, special conditions such as a high alcohol concentration are likewise required to efficiently bind and thus capture the small RNAs in the isolated total RNA. A commercial kit that is based on a respective phenol/chloroform method is the mirVana miRNA isolation kit (Ambion). After phenol/chloroform extraction, the protocol follows a fractionation strategy, wherein larger RNAs (more than 200 nucleotides) are bound in a first binding step to a nucleic acid binding solid phase at moderate alcohol concentrations (typically 25%). The flow-through comprises the small RNAs. Said small RNAs are captured from the flow-through by a second binding step wherein the alcohol concentration is raised to more than 50% (typically 55%) and the small RNA is bound to a second solid phase from which it can be eluted. Furthermore, a protocol is provided with the mirVana miRNA isolation kit wherein total RNA including small RNA is isolated from the aqueous phase that is obtained after the phenol/chloroform extraction. Here, the binding conditions are established by increasing the alcohol concentration to the required amounts to allow efficient binding of small RNA (typically 55%) in one step. Similar methods are also described in WO 2005/012523 and WO 2005/054466. However, also in these protocols an organic phenol/chloroform extraction step is usually performed in advance. Another phenol/chloroform based commercial product is the miRNeasy Mini kit (QIAGEN). It provides high quality and high yields of total RNA including small RNA from various different biological samples.

Generally, phenol based isolation procedures are relatively insensitive regarding the sample composition or the protein content. However, the sample is usually combined with 3 to 10 volumes of a phenol containing solution. This results in a relatively high sample volume that needs to be processed. Therefore, the initial sample volume is often rather small and lies in the range of 100 µl to 200 µl, seldom up to 500 µl. This is a disadvantage, in particular if the target small RNA is present in a low concentration in the initial sample. A further disadvantage is that phenol can be carried over into the eluate. Furthermore, removal of proteins is achieved by an organic phase extraction step, where each sample needs to be treated manually. Besides these technical difficulties and limitations, in particular the strong toxicity of phenol is perceived as disadvantage. Therefore, there is a great demand for phenol-free RNA isolation methods which allow to isolate total RNA including small RNA from various samples with high yield and quality.

Phenol-free methods for isolating RNA including small RNAs are also known in the prior art. To allow binding of total RNA including small RNA to a nucleic acid binding solid phase often a chaotropic salt and alcohol in a high concentration is used. Usually, the nucleic acid binding solid phase used comprises or consists of silica. However, the recovery of small RNA species like miRNA in methods that are based on binding the RNA to silica surfaces in the presence of alcohol and chaotropic substances require very high alcohol concentrations. Usually, approximately at least 50% alcohol is used in the binding mixture, usual ranges include 50-80% (v/v) alcohol in the binding mixture. However, when using respective phenol-free protocols that use high alcohol concentrations during binding, the total RNA yield and also the obtained small RNA yield is often reduced when processing protein-rich samples which could be a consequence of protein precipitations that are induced when alcohol is added in a high concentration to the disrupted sample. Some methods therefore limit the initial sample volume or reduce the alcohol concentration that is used during RNA binding (see above). Both measures allow to reduce the risk that the isolation is disturbed by precipitating proteins. However, the small nucleic acid isolation efficiency is reduced because binding is less efficient and/or the reduced input sample volume has the drawback that the overall concentration of small nucleic acids that can be isolated is reduced. Thus, generally, the performance of these protocols is unfortunately not comparable with phenol/chloroform based isolation methods. The problems are in particular observed with column based methods.

Other phenol-free methods include a protein precipitation step that is performed prior to the actual RNA isolation step. Protein precipitation is initiated by metal cations which is an established method for selectively precipitating proteins (see e.g. Lovrien, R. E. and Matulis, 2001 "Selective precipitation of proteins. Current Protocols in Proteins Science. 7:4.5.1-4.5.36). A respective method is described in EP 2 163 622. Here, the isolation of small RNA having a length of ≤200 nt from different sample types is disclosed. Metal cations are used to precipitate proteins and furthermore, larger nucleic acids are removed either prior to or during the protein precipitation step. The small RNA is then subsequently isolated from the obtained supernatant, by adding an organic solvent such as an apolar, protic organic solvent, e.g. THF, in a high concentration to the supernatant. This method selectively isolates small RNA, wherein the major amount of larger RNA (such as mRNA) and genomic DNA is lost and therefore, is not available for a subsequent analysis. This is a major drawback as some customers are interested in small RNA and in larger RNA such as mRNA and therefore, would need to perform an extra, separate isolation procedure in case also larger RNAs is of interest. Furthermore, a new sample or a new portion of an existing sample would need to be processed if after analysis of the small RNA an analysis of larger RNA is desired.

WO2016/009059 overcomes these drawbacks by incorporating an organic solvent selected from aprotic polar solvents and protic solvents into the precipitation mixture. This allows to provide a protein-depleted supernatant which comprises small as well as large RNA. Moreover, also DNA can be isolated from the supernatant.

It is the object of the present invention to provide a nucleic acid isolation method, in particular an RNA isolation method, which overcomes at least one of the above disadvantages of the prior art methods. In particular, it was the object of the present invention to provide a method that allows to isolate small RNA as well as large RNA, which avoids the use of phenol or proteolytic enzymes and provides good RNA yields with different sample types, including protein rich samples.

SUMMARY OF THE INVENTION

The inventors have found that a nucleic acid isolation method which comprises a metal cation induced protein precipitation step prior to isolating a nucleic acid from the protein depleted supernatant can be significantly improved by using a low concentration (less than 200 mM) of the metal cation precipitant in the precipitation mixture in combination with the use of a precipitation buffer having a pH of 4.0 or less. Surprisingly, it was found that using a low concentration of the metal cation precipitant in the precipitation mixture in combination with a low pH of the precipitation buffer allows to avoid the use of organic solvents during the protein precipitation step, which are described in WO 2016/009059 as mandatory to provide a protein-depleted supernatant which comprises small (less than 200 nt) as well as large RNA (at least 1000 nt). As is demonstrated by the examples of the present invention, the present method even though avoiding the use of an according organic solvent likewise provides after removal of the precipitate a protein-depleted supernatant is provided which comprises small (less than 200 nt) as well as large RNA (at least 1000 nt) and of course RNA of intermediate size if contained in the sample. All these RNA species can therefore be isolated from the protein-depleted supernatant, e.g. in form of total RNA or as one or more separate fractions enriched for the RNA of the desired size, respectively size range. Therefore, the method is particularly suitable for isolating various types of RNA. Furthermore, with the present method also DNA can be isolated from the obtained supernatant. Therefore, the present invention provides a method that allows to simultaneously isolate DNA and various types of RNA from biological sample, while in contrast to the method described in WO2016/009059 the present method does not require the use of organic solvents as part of the protein precipitation buffer to avoid co-precipitation of long RNA and DNA. The present invention therefore provides an improvement over WO2016/009059 in that the use of organic solvents during protein precipitation can be avoided. It was surprising that this can be achieved by lowering the concentration of metal cation precipitant in the precipitation mixture in combination with using a specific pH (4.0 or less) in the precipitation buffer. This in particular, as the known methods as described in WO2016/009059 and EP 2 163 622 teach higher metal cation precipitant concentrations in the precipitation mixture as preferred to improve the results. However, the use of lower concentrations of the metal cation precipitant in the precipitation mixture in combination with the specific pH conditions in the precipitation buffer as taught by the present invention allow to avoid the use of organic solvents during protein precipitation. Additionally, the use of lower metal cation precipitant concentrations in the precipitation mixture as taught herein reduces the risk that the metal cation precipitant is carried over in the eluates during nucleic acid isolation. This is advantageous, because metal cation precipitant such as zinc can inhibit downstream reactions such as e.g. PCR based methods. Therefore, the present invention provides an improved nucleic acid isolation method which also gives the user flexibility with respect to the nucleic acid to be isolated.

According to a first aspect, a phenol-free method for isolating a nucleic acid from a sample is provided, said method comprising the following steps:
a) adding a precipitation buffer to a sample to prepare an acidic precipitation mixture wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM
and precipitating proteins;
b) separating the precipitate from the supernatant, wherein the supernatant comprises small RNA having a length of less than 200 nt and large RNA having a length of at least 1000 nt; and
c) isolating a nucleic acid from the supernatant.

The method is particularly suitable for isolating RNA as target nucleic acid from a sample, in particular a disrupted biological sample. The examples show that the present invention provides a highly efficient method for isolating RNA with good yield using a method that does not comprise a phenol-based extraction step. The present method provides comparable results even though no phenol or water-insoluble organic solvents such as chloroform are used for extracting proteins. In addition, the use of organic solvents selected from aprotic polar solvents and protic solvents during the precipitation step can be avoided (such organic solvents are used e.g. in WO2016/009059). Therefore, the use of organic solvents can be avoided during the precipitation step. The method provides after the metal cation induced precipitation step a protein-depleted supernatant which comprises small RNA, large RNA and in embodiments genomic DNA. One or more of the contained nucleic acid types can then be isolated from the supernatant. Therefore, the method allows e.g. the isolation of small as well as large RNA with good yield, thereby advantageously providing a method which provides more flexibility to the user. In addition, the use of the low concentration of metal cation precipitant in the precipitation mixture as taught herein reduces the risk that down-stream analytic methods, in particular enzyme based methods such as polymerase based methods, are inhibited by carryover of metal cation precipitant. The present invention makes a major contribution to the art and also significantly improves existing phenol-free, precipitation based RNA isolation methods. Furthermore, the nucleic acid isolation method according to the present invention can be easily implemented into existing protocols which either aim at the isolation of small and/or large RNA or which aim at the parallel isolation of such RNA and also DNA from various samples, including protein rich samples such as blood, plasma or serum.

According to a second aspect, a precipitation buffer for precipitating proteins is provided comprising and at least one metal cation precipitant and at least one buffering agent, wherein the precipitation buffer has a pH value of 4 or less and wherein the precipitation buffer does not comprise an organic solvent selected from aprotic polar solvents and protic solvents.

Said precipitation buffer can be used e.g. for precipitating proteins from a sample, such as a disrupted biological sample, thereby providing after separation of the precipitate a protein-depleted supernatant which comprises small RNA having a length of less than 200 nt and large RNA having a length of at least 1000 nt and also RNA of intermediate size if contained in the sample. The contained RNA can then be isolated from the supernatant e.g. in form of total RNA or as one or more separate fractions enriched for RNA of a certain size, respectively size range (e.g. less than 200 nt or larger than 200 nt). Said precipitation buffer may be comprised in a kit for isolating nucleic acids such as in particular RNA.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides an improved protein precipitation based method for processing a RNA containing sample, which provides after precipitation a protein-depleted supernatant which comprises small as well as large RNA and also DNA. One or more of the contained nucleic acid types can subsequently be isolated from the supernatant. Thus, one method is provided that can be used for the isolation of different nucleic acids.

A. Method for Isolating a Nucleic Acid from a Sample

According to a first aspect, a phenol-free method for isolating a nucleic acid from a sample is provided, said method comprising the following steps:
a) adding a precipitation buffer to a sample, preferably a disrupted biological sample, to prepare an acidic precipitation mixture
wherein said precipitation buffer comprises a metal cation precipitant and a buffering agent, has a pH value of 4.0 or less and does not comprise an organic solvent selected from aprotic polar solvents and protic solvents and
wherein the acidic precipitation mixture comprises the metal cation precipitant in a concentration of less than 200 mM
and precipitating proteins;
b) separating the precipitate from the supernatant, wherein the supernatant comprises small RNA having a length of less than 200 nt and large RNA having a length of at least 1000 nt; and
c) isolating a nucleic acid from the supernatant.

Subsequently, we will explain each step and preferred embodiments thereof in detail.

Step a)—Protein Precipitation

In step a), a precipitation mixture containing the sample is prepared and proteins are precipitated. The sample is preferably a biological sample and may be e.g. a disrupted sample if sample disruption is necessary to release the nucleic acids. As is described subsequently, sample disruption may also occur during the protein precipitation step. Sample disruption e.g. by using a lysis reagent comprising a chaotropic agent is as explained subsequently advantageous to initially denature proteins such as nucleases, to dissociate protein-nucleic acid complexes, to lyse exosomes and other extracellular vesicles comprising nucleic acids and/or to assist preparing suitable conditions for subsequently binding nucleic acids in step c). An according sample disruption step is therefore preferably performed in advance to step a). This is in particular when processing biological samples rich in proteins such as e.g. plasma, serum or whole blood. To initiate precipitation, a precipitation buffer is added to the sample to prepare an acidic precipitation mixture. The precipitation buffer comprises a metal cation precipitant (preferably zinc chloride) and a buffering agent and has a pH value of 4.0 or less. In contrast to the prior art, the precipitation buffer does not comprise an organic solvent selected from aprotic polar solvents and protic solvents. No organic solvents are required. Thereby, an acidic precipitation mixture is provided which comprises the metal cation precipitant contained in the precipitation buffer in a concentration of less than 200 mM. These precipitation conditions allow to obtain a protein-depleted supernatant that comprises not only small RNA having a length of less than 200 nt but additionally comprises large RNA having a length of at least 1000 nt. Of course, the supernatant may also comprise RNA species of intermediate size if comprised in the sample. That not only small but also larger RNA species are comprised in the protein-depleted supernatant is advantageous, because the applicability of the method is broad and the user may isolate different types of RNA. Furthermore, also DNA can be isolated from the supernatant as is demonstrated in the examples.

The use of a metal cation precipitant for precipitating proteins is known in the prior art and suitable metal cation precipitants are also described (see e.g. Lovrien, R. E. and Matulis, 2001 "Selective precipitation of proteins. Current Protocols in Proteins Science. 7:4.5.1-4.5.36 or EP 2 163 622 and WO2016/09059). Any metal cation capable of acting as a protein precipitant can be used in conjunction with the invention and examples include but are not limited to cations of Cu, Cd, Hg, Pb, Zn, Fe and Al. Also combinations of metal cation precipitants can be used. Preferably, the metal cation precipitant is selected from $Zn^{2+}$, $Cu^{2+}$ and $Al^{3+}$, more preferably it is $Zn^{2+}$. As known from the prior art (see e.g. WO2016/009059) and also demonstrated by the examples, these metal cation precipitants have advantages, because $Zn^{2+}$, $Cu^{2+}$ and $Al^{3+}$ initiate protein precipitation very rapidly and are also effective in low concentrations. The use of $Zn^{2+}$ is particularly preferred.

The metal cation precipitant is added via the precipitation buffer, which preferably comprises a dissolved salt of the metal cation precipitant. E.g. halogenide salts such as chloride salts may be used. The use of zinc chloride is particularly preferred in the present method. Thus, all disclosures described in this application for the metal cation precipitant in general, specifically apply and particularly refer to the preferred embodiment zinc chloride even if not explicitly stated. The precipitation buffer preferably is an aqueous solution.

The acidic precipitation mixture that is provided in step a) comprises the metal cation precipitant introduced by the precipitation buffer in a concentration of 200 mM or less. As is known from the prior art (see e.g. WO2016/009059), a concentration of approx. 50 mM zinc chloride in the precipitation mixture is already sufficient to precipitate proteins. However, the prior art preferred the use of higher concentrations of at least 200 mM and higher. As is demonstrated by the present examples, using a lower concentration of metal cation precipitant such as zinc chloride is advantageous, because in combination with a low pH of the precipitation buffer it allows to omit an organic solvent selected from aprotic polar solvents and protic solvents during precipitation while still providing a protein-depleted supernatant that comprises small as well as large RNA. Thus, the present method does not comprise a step of adding an organic solvent selected from aprotic polar solvents and protic solvents to the sample to prepare the precipitation mixture. The precipitation mixture does not comprise an organic solvent selected from aprotic polar solvents and protic solvents. According organic solvents are used in described in WO2016/009059, herein incorporated by reference regarding the details of the organic solvents that are avoided by the present method during precipitation. Examples of aprotic polar solvents described in WO2016/009059 include sulfoxides such as dimethylsulfoxide (DMSO), ketones such as acetone, nitriles such as acetonitrile, cyclic ethers such as tetrahydrofurane (THF) and 1,4 dioxane, lactames such as 1-methyl-2-pyrolidone (NMP) and tertiary carboxylic acid amides such as dimethyl-formamide (DMF). Such aprotic polar organic solvents are advantageously not used in the present method to prepare the precipitation mixture and to provide a protein-depleted supernatant which comprises small RNA, large RNA and additionally high molecular weight nucleic acids such as in particular genomic DNA. Examples of polar protic solvents described in WO2016/009059 include linear or branched C1-05 alcohols, in particular water-miscible alcohols such as isopropanol, ethanol or methanol. Such polar protic organic solvents are advantageously not used in the present method to prepare the precipitation mixture and to provide the protein-depleted supernatant which comprises small RNA and large RNA in large amounts and of course also RNA of intermediate size if contained in the sample. The precipitation mixture does preferably not contain any organic solvents.

The acidic precipitation mixture provided in step a) may comprise the metal cation precipitant, preferably zinc chloride, in a concentration of 185 mM or less, 180 mM or less, 175 mM or less, 170 mM or less, 165 mM or less, 160 mM or less, 155 mM or less, 150 mM or less, 145 mM or less or 140 mM or less. The use of corresponding low concentrations in the precipitation mixture is advantageous because it reduces the risk that the metal cation precipitant is accidently carried over in downstream reactions. Particularly preferred is a concentration of 150 mM or less, 145 mM or less or 140 mM or less. As discussed, zinc chloride is preferably used. The acidic precipitation mixture provided in step a) may comprise the metal cation precipitant in a concentration of at least 50 mM, at least 60 mM, at least 65 mM, at least 70 mM, at least 75 mM, at least 80 mM, at least 85 mM, at least 90 mM, at least 95 mM or at least 100 mM. Preferred is a concentration of at least 80 mM or at least 90 mM. As discussed, zinc chloride is preferably used.

According to one embodiment, the acidic precipitation mixture provided in step a) comprises the metal cation precipitant in a concentration selected from 50 mM to 175 mM, 60 mM to 170 mM, 65 mM to 165 mM, 70 mM to 160 mM, 75 mM to 155 mM, 80 mM to 150 mM, 85 mM to 145 mM and 90 mM to 140 mM. Particularly preferred is a concentration selected from 75 mM to 160 mM, 80 mM to 150 mM and 90 mM to 140 mM. As discussed, zinc chloride is preferably used. These concentration ranges are in the present method particularly suitable to effect protein precipitation while providing a supernatant that comprises small as well as large RNA in high amounts. These concentration ranges are particularly useful if $Zn^{2+}$ is used as metal cation precipitant. As discussed, the precipitation buffer preferably comprises zinc chloride so that these concentration ranges in the precipitation mixture in particular apply to zinc chloride.

According to one embodiment, the mentioned concentrations refer to the overall concentration of metal cation precipitants in the precipitation mixture if two or more metal cation precipitants are added to provide the precipitation mixture. According to one embodiment, a single metal cation precipitant, preferably $Zn^{2+}$ e.g. zinc chloride, is comprised in the precipitation buffer and hence is used to prepare the precipitation mixture. This embodiment was also used in the examples.

The precipitation buffer that is added to provide the acidic precipitation mixture may have a pH value that is selected from 2.5 to 4, 2.75 to 3.9, 2.8 to 3.9, 3.0 to 3.9, 3.1 to 3.9, 3.2 to 3.9, 3.3 to 3.9, 3.4 to 3.9 and 3.5 to 3.9. Also, pH values selected from 3.3 to 3.8, 3.4 to 3.8 and 3.5 to 3.8 can be used. As is demonstrated by the examples, using an according acidic precipitation buffer is advantageous. The precipitation buffer is preferably suitable to establish and/or maintain a corresponding pH value in the precipitation mixture.

According to one embodiment, the precipitation buffer has a pH value in the range of 2.75 to 4.0 and the acidic precipitation mixture provided in step a) comprises the metal cation precipitant in a concentration in a range of 50 mM to 175 mM. In some embodiments, the precipitation buffer has a pH value in the range of 3.0 to 4.0, for example 3.3 to 3.9, 3.4 to 3.9 or 3.5 to 3.9, and the acidic precipitation mixture provided in step a) comprises the metal cation precipitant in a concentration in a range of 50 mM to 175 mM. In some embodiments, the precipitation buffer has a pH value in the range of 2.75 to 4.0, and the acidic precipitation mixture provided in step a) comprises the metal cation precipitant in a concentration in a range of 60 mM to 170 mM, for example 70 mM to 160 mM, 80 mM to 150 mM or 90 mM to 140 mM. In some embodiments, the precipitation buffer has a pH value in the range of 3.5 to 3.9, and the acidic precipitation mixture provided in step a) comprises the metal cation precipitant in a concentration in a range of 50 mM to 175 mM, for example 60 mM to 170 mM, 70 mM to 160 mM, 80 mM to 150 mM or 90 mM to 140 mM. In some embodiments, the precipitation buffer has a pH value in the range of 2.75 to 4.0, for example 3.0 to 4.0, 3.3 to 3.9, 3.4 to 3.9 or 3.5 to 3.9, and the acidic precipitation mixture provided in step a) comprises the metal cation precipitant in a concentration in a range of 90 mM to 140 mM.

In some embodiments, the precipitation buffer has a pH value in the range of 3.0 to 4.0, and the acidic precipitation mixture provided in step a) comprises the metal cation precipitant in a concentration in a range of 60 mM to 170 mM. In some embodiments, the precipitation buffer has a pH value in the range of 3.3 to 3.9, and the acidic precipitation mixture provided in step a) comprises the metal cation precipitant in a concentration in a range of 70 mM to 160 mM. In some embodiments, the precipitation buffer has a pH value in the range of 3.4 to 3.9, and the acidic precipitation mixture provided in step a) comprises the metal cation precipitant in a concentration in a range of 80 mM to 150 mM. In some embodiments, the precipitation buffer has a pH value in the range of 3.5 to 3.9, and the acidic precipitation mixture provided in step a) comprises the metal cation precipitant in a concentration in a range of 90 mM to 140 mM.

The precipitation buffer comprises a buffering agent to maintain the acidic pH of the precipitation buffer which is important for the present method. Different buffering agents are suitable and may be used (see also WO2016/009059). Also combinations of buffering agents may be used. According to one embodiment, the buffering agent is or is derived from a carboxylic acid. Carboxylic acids include mono-, di- or tri carboxylic acids. Preferably, the buffering agent is acetic acid or citric acid, respectively is an acetate or citrate. Acetate and citrate can be added in form of different salts. E.g. an alkali metal salt such as a sodium or potassium salt may be used. According to one embodiment sodium acetate is used as buffering agent. According to one embodiment, the precipitation buffer comprises the buffering agent in a concentration selected from 300 mM to 3M, 600 mM to 2.75M, 900 mM to 2.5M, 1.2M to 2.4M, 1.4M to 2.3M and 1.5M to 2.25M. Particularly preferred are carboxylic acid salts such as acetate or citrate salts, e.g. alkali metal salts which may be used in the before mentioned concentration ranges. Particularly preferred is a concentration that lies in the range of 1.6M to 2.5M, 1.8M to 2.3M or 1.9 mM to 2.2M. According to one embodiment, the mentioned concentrations refer to the overall concentration of buffering agents in the precipitation buffer if two or more buffering agents are comprised or if the buffing agent is added to the buffer in two or more different forms, such as sodium acetate and acetic acid.

Using a precipitation buffer that has and maintains a respective acidic pH in the precipitation mixture provides advantageous results, in particular when processing protein rich samples such as plasma or serum. The pH value of the precipitation mixture is acidic. It may be affected by the biological sample and may be ≤6, ≤5.75, ≤5.5, ≤5.25 or ≤5. This also depends on the volume of precipitation buffer used. Suitable ranges include 3 to 6.5, 3.5 to 6.0, 4.0 to 5.5, or 4.5 to 5.25.

According to one embodiment, the precipitation mixture comprises the buffering agent in a concentration that lies in a range selected from 25 mM to 500 mM, 50 mM to 400 mM, 75 mM to 300 mM, 100 mM to 250 mM and 125 mM to 200 mM. These concentration ranges are particularly suitable for carboxylic acids, respectively salts of carboxylic acids such as sodium acetate. A concentration that lies in the range of 100 mM to 200 mM or 125 mM to 175 mM achieves particularly good results.

The use of a precipitation buffer is convenient, as the agents required to achieve protein precipitation and hence protein depletion while maintaining small as well as large RNA in the supernatant are contained in one buffer that is added to the sample. The sample is in one embodiment a disrupted sample. The composition of the precipitation buffer is such that when adding the intended volume of precipitation buffer to a certain volume of the sample, which may be a disrupted sample, a precipitation mixture is provided that comprises the metal cation precipitant in a concentration as described above. In certain embodiments, the sample, which may be a disrupted sample, is mixed with the precipitation buffer in a ratio in the range of from 1:1 to 1:30 (precipitation buffer:sample). In particular, the ratio may lie in the range of from 1:3 to 1:25, such as 1:6 to 1:20, 1:8 to 1:17, 1:10 to 1:15, or 1:12 to 1:14 (precipitation buffer: sample). In some embodiments, the sample is mixed with the precipitation buffer in a ratio in the range of from 1:11 to 1:15, especially from 1:12 to 1:14 (precipitation buffer: sample). In specific embodiments, the precipitation buffer is added to the sample, which may be a disrupted sample, in a ratio of about 1:13 (precipitation buffer:sample). In some embodiments, a disruption buffer for disrupting the sample may be added to the sample before the precipitation buffer is added. In these embodiments, the ratio of the precipitation buffer to the sample may be calculated using the volume of the disrupted sample, i.e. the volume of the initial sample and the disruption buffer, as the sample volume. Advantageously, the present invention allows to use a low volume of precipitation buffer compared to a large volume of the sample, which preferably is a disrupted sample. This allows to increase the processing volume of the sample. This is particularly advantageous if processing cell-depleted or cell-free biological samples, such as plasma, serum or urine, in order to isolate cell-free or circulating nucleic acids from such biological samples. Cell-free nucleic acids such as RNA and DNA are usually present in low amounts in such samples so that it is advantageous to process a large sample volume.

The precipitation buffer that is added to the sample, which according to one embodiment is a disrupted sample, to establish the conditions of the precipitation mixture preferably comprises the metal cation precipitant in form of a dissolved salt. E.g. halogenide salts such as chloride salts can be used. The metal cation precipitant, preferably present in form of a dissolved salt, may be comprised in the precipitation buffer in a concentration selected from 250 mM to 3M, 500 mM to 2.8M, 0.75M to 2.7M, 1M to 2.6M, 1.2M to 2.5M, 1.3M to 2.25M and 1.6M to 2M. Suitable metal cation precipitants were described above, preferably a metal cation precipitant selected from $Zn^{2+}$, $Cu^{2+}$ and $Al^{3+}$ is used. Most preferred is $Zn^{2+}$ which can be used e.g. in form of zinc chloride. As is demonstrated by the examples, using a precipitation buffer that comprises the metal cation precipitant in a respective concentration provides good results. Even though the present invention uses a low metal cation precipitant concentration in the precipitation mixture it is nevertheless possible and also advantageous to use a high concentration of the metal cation precipitant in the precipitation buffer that is added to the sample. This allows to use lower amounts of the precipitation buffer to prepare the precipitation mixture. Using lower amounts of precipitation buffer is advantageous, because the overall volume of precipitation mixture to be processed is thereby reduced. This moreover allows to increase the volume of the sample while maintaining the processing volume of the precipitation mixture. This is particularly advantageous when intending to isolate mRNA from cell-free of cell-depleted biological samples (such as e.g. plasma or serum), because such samples often contain only low amounts of mRNA. Therefore, the processing of a sample volume of at least 500 μl, at least 750 μl, at least 800 μl, at least 900 μl or at least 1000 μl is advantageous, in particular when intending to capture mRNA from the protein-depleted supernatant.

When the precipitation mixture is provided by addition of the precipitation buffer, the proteins contained in the sample are precipitated. Precipitation can be assisted e.g. by agitation. Agitation includes but is not limited to vortexing, shaking, inverting and pipetting up and down. Furthermore, the sample may be cooled, e.g. stored on ice as is also described in the examples.

As described above, the precipitation mixture is prepared by adding the precipitation buffer described above to the nucleic acid containing sample. Non-limiting examples of suitable RNA containing biological samples are also described below. The present method is particularly suitable for isolating RNA from protein rich samples, such as e.g. plasma or serum. Where necessary, the sample is disrupted in advance. Therefore, according to one embodiment, the method encompasses a step of disrupting a sample. Thereby, nucleic acids such as in particular RNA are released and become better accessible for the subsequent nucleic acid isolation step.

Different methods can be used in order to disrupt the sample. The term "disrupting" or "disruption" is used herein in broad sense and in particular encompasses the lysis of a sample. In a respective lysis step, biomolecules such as in particular RNA are released from cells or can be freed from other sample components such as e.g. proteins, thereby rendering the RNA accessible for isolation. Sample disruption e.g. by using a lysis reagent comprising a chaotropic agent is advantageous to initially denature proteins such as nucleases, to dissociate protein-nucleic acid complexes, to lyse exosomes and other extracellular vesicles comprising nucleic acids and/or to assist preparing suitable conditions for subsequently binding nucleic acids in step c). Herein, it is referred to a respective disruption step also generally as lysis step, irrespective of whether biomolecules such as in particular nucleic acids are released from cells or whether the lysis is performed in order to release biomolecules such as nucleic acids e.g. from proteins or other substances comprised in the sample. Hence, the sample may comprise cells or may comprise no or only minor amounts of cells as is e.g. the case with blood plasma.

Different methods can be used in order to lyse the sample and suitable lysis methods are well-known in the prior art. Preferably, the sample is contacted for disruption, respectively lysis, with one or more lysing agents. These can be contained in a disruption reagent such as a lysis buffer. RNA should be protected during lysis from degradation by nucleases. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. According to one embodiment, at least one chaotropic agent, such as preferably at least one chaotropic salt, is used for lysing and hence disrupting the sample. Suitable chaotropic agents and in particular suitable chaotropic salts are known to the skilled person and are also described herein. As is described herein, using a chaotropic salt for lysis has the advantage that it allows to introduce a chaotropic salt which may additionally support establishing suitable nucleic acid binding conditions in step c).

As is known from the prior art (see WO2016/009059), sample disruption may occur prior to addition of the metal cation precipitant but may also occur at the same time respectively stage when the precipitation mixture is prepared. Depending on the sample to be processed, a lysis/binding composition may also be added after preparation of the precipitation mixture. This is less preferred though as it may reduce the RNA yield when processing complex samples such as blood or serum.

Thus, according to one embodiment, the sample is disrupted at the same time respectively stage when the precipitation buffer is added in step a). According to this embodiment, a phenol-free method for isolating a nucleic acid from a sample is provided, which comprises the following steps:
a) adding a precipitation buffer and at least one disruption reagent to the sample to disrupt the sample and to prepare an acidic precipitation mixture
wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM and comprises the disruption reagent and precipitating proteins;
b) separating the precipitate from the supernatant, wherein the supernatant comprises small RNA having a length of less than 200 nt and large RNA having a length of at least 1000 nt; and
c) isolating a nucleic acid from the supernatant.

Suitable disruption reagents such as lysis buffers that can be used are well known to the skilled person and are also described herein. Such disruption reagent may be added e.g. separately from the precipitation buffer or may be mixed with the precipitation buffer in advance so that then a mixture of the precipitation buffer and the disruption reagent is added to the sample in step a). According to one embodiment, the disruption reagent comprises a chaotropic salt. Suitable examples are known and also described herein.

According to a preferred embodiment, the sample is disrupted prior to adding the metal cation precipitant and the organic solvent in step a). According to this embodiment, a phenol-free method for isolating a nucleic acid from a sample is provided, which comprises the following steps:
x) disrupting a sample;
a) adding a precipitation buffer to the disrupted sample to prepare an acidic precipitation mixture
wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM and precipitating proteins;
b) separating the precipitate from the supernatant, wherein the supernatant comprises small RNA having a length of less than 200 nt and large RNA having a length of at least 1000 nt; and
c) isolating a nucleic acid from the supernatant.

According to one embodiment, for disrupting a sample in step x), a disruption composition is provided which comprises the sample to be disrupted and in addition thereto a chaotropic agent, preferably a chaotropic salt, in a concentration selected from the group consisting of 0.5M to saturation, 0.75M to 4M, 0.8M to 3.5M, 1M to 3M, 1M to 2.5M and 1M to 2M. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Such chaotropic salts can be provided e.g. as sodium or potassium salts. Preferably, the chaotropic salt is GTC (GITC) or an equally strong chaotropic salt. Respective strong chaotropic salts are advantageous as they may also efficiently protect the RNA comprised in the composition from enzymatic degradation. Also urea may be used to support the disruption of the sample. According to one embodiment, the disruption composition is provided in step x) and hence prior to adding the precipitation buffer in step a) to said disruption composition which comprises the disrupted sample.

Furthermore, during lysis, also one or more further additives can be added e.g. selected from detergents, e.g. non-ionic detergents, chelating agents, nuclease inhibitors, in particular RNase inhibitors or DNase inhibitors (if the parallel isolation of RNA and DNA is intended) and the like. Respective additives that can be used to support the lysis of a sample and to protect the released nucleic acids, in particular the released RNA, are well-known in the prior art and thus, do not need to be described in detail herein.

The disrupted sample obtained from the sample in step x) may also optionally be further processed prior to preparing the precipitation mixture in step a). For example, the lysate can be homogenized; homogenization may also occur during the disruption/lysis process itself. Furthermore, the lysate can be cleared in order to remove cell debris. Lysate clearing methods may involve filtration and/or binding the cell debris and other contaminants to appropriate surfaces, such as for example surfaces carrying ionic groups, in particular anionic groups such as carboxyl groups.

The method of the present invention may be combined with a proteolytic digest. Even if a proteolytic digest is performed, the precipitation based method of the invention can still improve the results by depleting residual proteins. The term "protein" as used herein also encompasses peptides. However, it is an advantage of the present invention that it does not require a time consuming proteolytic enzymatic digestion step. Therefore, according to one embodiment, disruption of the sample does not involve the use of a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like.

Step b)—Removal of the Precipitate

In step b) the formed precipitate is separated from the remaining sample, herein referred to as "supernatant". Separation can be assisted by various means such as e.g. sedimentation, centrifugation or filtration. The term "supernatant" is used herein in particular to describe the precipitation mixture from which the formed precipitate was removed. The term "supernatant" is therefore not limited to a specific precipitate depleted precipitation mixture that was obtained by a certain mode of precipitate separation. Thus, the term "supernatant" e.g. encompasses embodiments wherein the precipitate is collected at the bottom of a vessel and wherein the remaining sample is removed as supernatant as well as embodiments wherein the precipitation mixture is passed through a filter to remove the formed precipitate and recover the remaining sample in form of a flow-through.

As is demonstrated by the examples, due to the conditions used in the method according to the invention, the obtained supernatant comprises small RNA having a length of less than 200 nt and in addition thereto large RNA having a length of at least 1000 nt. Of course, also RNA of intermediate size is comprised in said supernatant if comprised in the original sample. According to one embodiment, the obtained supernatant comprises at least 60%, at least 65%, at least 70%, at least 75% or at least 80% of the RNA molecules having a length of at least 1000 nt that are contained in the original sample. It was also found that the large RNA recovery rates are as high. Thus, in contrast to prior art precipitation based methods, the present method allows the recovery and isolation of large RNA molecules with good yield while allowing to avoid the use of an organic solvent selected from aprotic polar solvents and protic solvents. Additionally, high molecular weight nucleic acids such as genomic DNA can be comprised in said supernatant and isolated therefrom, as it is demonstrated in the examples.

Step c)—Isolating a Nucleic Acid from the Supernatant

In step c), a nucleic acid is isolated from the obtained supernatant. The nucleic acid may be RNA, DNA or both. For isolating the one or more target nucleic acids (e.g. RNA and/or DNA) of interest from the obtained supernatant, methods known in the prior art may be used. Examples of suitable isolation methods include but are not limited to silica-based purification methods, magnetic particle-based purification methods, chromatography based purification procedures, anion-exchange chromatography (using anion-exchange surfaces, such as columns or magnetic particles), precipitation and combinations thereof. Preferably, one or more of the target nucleic acids such as RNA and/or DNA is isolated from the supernatant by binding the nucleic acid to a solid phase using appropriate binding conditions. The solid phase may e.g. provide a silica binding surface or may carry anion exchange functional groups which can bind the nucleic acid of interest. With respect to the latter embodiment, e.g. isolation methods that are based on the charge-switch principle may be used.

Preferably, at least RNA is isolated from the supernatant. For isolating RNA from the obtained supernatant, methods known in the prior art can be used. The method according to the invention has the advantage that the supernatant comprises small as well as large RNA. Therefore, the user may, depending on the target RNA of interest, isolate either small RNA, large RNA or both from the supernatant. Small and large RNA may be isolated in separate fractions or may be isolated in form of total RNA or total nucleic acids from the supernatant. Of course, also RNA of intermediate size is comprised in the supernatant if comprised in the sample and can be isolated e.g. together with the large RNA and/or the small RNA. DNA can be co-isolated.

Preferably, the nucleic acid, in particular RNA, is isolated from the supernatant by binding it to a nucleic acid binding solid phase in the presence of an organic solvent such as an alcohol. Binding to the solid phase can be enhanced in the presence of a chaotropic salt in the binding mixture. Non-limiting embodiments are described subsequently.

The alcohol may be a branched or unbranched aliphatic alcohol with 1 to 5 carbon atoms and may be selected from methanol, ethanol, propanol, isopropanol and butanol and mixtures thereof. Also mixtures of alcohol can be used. The skilled person is familiar with the use of according alcohols to establish RNA and/or DNA binding conditions. Preferably, isopropanol and/or ethanol is used as alcohol to establish the binding conditions. These alcohols are commonly used to isolate small and large RNA from disrupted samples. DNA can also be isolated under these conditions. Particularly preferred is the use of isopropanol. It was found that the use of isopropanol inter alia reduces the risk that the metal cation precipitant is carried over into the eluates. As discussed above, this should be avoided as several downstream methods such as e.g. PCR based methods are inhibited by metal cation precipitants such as e.g. zinc chloride.

According to one embodiment, nucleic acids are isolated from the supernatant, wherein said nucleic acids comprise or consist of small as well as large RNA and RNA of intermediate size. In this embodiment, step c) preferably comprises:
aa) adding at least one alcohol to the supernatant to provide a binding mixture which comprises the alcohol in a concentration ≥35%, preferably ≥40%, more preferred ≥45%;
bb) binding nucleic acids contained in the binding mixture to a silicon containing nucleic acid binding solid phase, wherein after step bb), at least large and small RNA is bound to the solid phase;
cc) optionally washing the bound nucleic acids; and
dd) optionally eluting nucleic acids from the solid phase.

It is a well-established principle that large RNA as well as small RNA and of course RNA of intermediate size can bind to a nucleic acid binding solid phase in the presence of a high concentration of alcohol. Therefore, the present method allows in this embodiment to isolate total RNA which comprises small RNA, large RNA and RNA of intermediate size. Respective methods are also described in the background of the invention. As described herein, also DNA may be comprised in the isolated nucleic acids. It is, however, also within the scope of the invention to isolate total RNA, depleted of DNA, from the supernatant.

Using an alcohol concentration of at least 35%, preferably at least 40%, more preferred at least 45% or at least 50% in the binding mixture during the binding step has the effect that binding conditions for RNA are established that allow to bind small RNA to the nucleic acid binding solid phase. Here, it was found that also lower alcohol concentrations of 35% can be used in conjunction with the present method than are commonly used in the prior art to achieve binding of small RNA to the solid phase. Of course, also longer RNA molecules can bind under these conditions and thus are captured.

Due to the protein precipitation step that is performed in advance, a high alcohol concentration can be used in the binding mixture because the risk is reduced that proteins precipitate during the binding step and e.g. clog the nucleic acid binding solid phase or otherwise interfere with nucleic acid binding. This is beneficial with respect to the yield. The alcohol concentration in the binding mixture may be ≥40% (v/v), ≥45% (v/v) or ≥50% (v/v). In embodiments, the alcohol concentration is 70% (v/v) or less, 65% (v/v) or less or 60% (v/v) or less. Suitable ranges for the alcohol concentration in the binding mixture include but are not limited to ≥35% (v/v) to ≤80% (v/v), ≥35% (v/v) to ≤70% (v/v), ≥40% (v/v) to ≤65% (v/v), ≥45% (v/v) to ≤60% (v/v) and ≥45% (v/v) to ≤55% (v/v). An alcohol concentration of approx. 50% (v/v) is particularly preferred. Respective alcohol concentrations can be used in step aa). As discussed, ethanol and isopropanol are preferred, with isopropanol being most preferred. Higher alcohol concentrations are beneficial for binding small RNA. However, very high alcohol concentrations increase the risk that traces of the metal cation precipitant and/or other contaminations are carried over into the eluate. Therefore, an alcohol concentration of ≥45% (v/v) to ≤55% (v/v), in particular about 50% (v/v) is particularly preferred.

According to one embodiment, binding of the nucleic acid such as in particular RNA to a nucleic acid binding solid phase is enhanced by incorporating a chaotropic salt in the binding mixture. Suitable concentrations for chaotropic salts are known to the skilled person and are described herein.

According to one embodiment, the binding mixture of step aa) comprises a chaotropic salt in a concentration which lies in a range of 0.1M up to the saturation limit. The concentration may be selected from 0.2M to 5M, 0.25M to 4.5M, 0.3M to 4.25M, 0.35 to 4M and 0.4M to 3.75M. Higher concentrations of chaotropic salts can be favourable to increase the yield of bound nucleic acids, such as in particular RNA. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Also mixtures of chaotropic salts may be used. Such chaotropic salts can be provided e.g. as sodium or potassium salts. Preferably, the chaotropic salt is GTC or GITC or an equally strong chaotropic salt. The chaotropic salt present in the binding mixture may have been introduced during lysis, as the use of chaotropic agents, in particular chaotropic salts, for lysis is preferred for disrupting the sample. Details were described above. This procedure was also used in the examples. A chaotropic salt may also be added during step c) either to introduce a chaotropic salt into the binding mixture or to increase the concentration of the chaotropic salt during the nucleic acid binding step. Thus, it is also within the scope of the present invention to increase the concentration of chaotropic salt for binding, by adding a further amount of chaotropic salt in the isolation step c). Furthermore, additional additives can be added to improve nucleic acid binding, such as e.g. detergents.

In step bb), small and large RNA and RNA of intermediate size contained in the binding mixture resulting from step aa) are bound to a nucleic acid binding solid phase. Solid phases suitable for nucleic acid binding are known to the skilled person; exemplary suitable nucleic acid binding solid phases are also described below. According to one embodiment, the binding mixture resulting from step aa) is contacted with a solid phase in step bb). This embodiment is particularly suitable if a nucleic acid binding phase comprised in a column is used. If a column based procedure is used, a nucleic acid binding solid phase may be used in step bb) in order to bind nucleic acids, including small RNA, to the solid phase. In case particles are used, they may also be present already in step aa) or may be introduced in step bb).

The bound nucleic acids may optionally be washed in step cc). For this purpose common washing solutions may be used. According to one embodiment, the solutions used for washing comprises at least one chaotropic agent and/or at least one alcohol. For example, a first washing solution comprises a chaotropic agent and a second washing solution comprises an alcohol. Chaotropic agents that can be used in the washing solutions include but are not limited to chaotropic salts such as guanidinium hydrochloride, guanidinium thiocyanate, guanidinium isothiocyanate and sodium iodide. Other chaotropic salts are also described above. As alcohol, short chained branched or unbranched alcohols with preferably 1 to 5 carbon atoms can be used for washing, respectively in the washing solution. Examples are methanol, ethanol, propanol, isopropanol and butanol. Preferably, isopropanol and/or ethanol are used. However, also washing solutions without a chaotropic agent can be used. The washing step also allows to influence the type of isolated nucleic acids. E.g. if intending to isolate total RNA depleted of DNA.

An example of a suitable washing solution which can be used either alternatively or also in addition to the washing solutions described above comprises an alcohol and a buffer. Suitable alcohols are described above. Preferably, isopropanol or ethanol, most preferred ethanol is used for this washing step. Preferably, ethanol is used in a concentration of at least 60% (v/v), at least 70% (v/v), preferably at least 80% (v/v). According to one embodiment, the solution used for washing comprises at least one chaotropic agent, at least one alcohol, at least one detergent and/or at least one buffering agent. Suitable buffering agents such as Tris or citrate can be used; suitable buffering agents are also known to the skilled person.

Either prior to or subsequent to the optional one or more washing steps described above, a DNase digest may be performed. Such DNase digest may be performed e.g. while the nucleic acid is bound to the nucleic acid binding solid phase. An according step is advantageous if intending to isolate total RNA depleted of DNA. Thereby, the amount of genomic DNA contaminations in the isolated RNA can be reduced if only RNA is the nucleic acid of interest. Suitable embodiments for performing a respective DNase digest are described herein and are also known in the prior art. A respective DNase digestion step is optional. The conditions used for performing the DNase digest while the RNA is bound to the nucleic acid binding solid phase can result in that RNA and in particular small RNA is partially released from the nucleic acid binding solid phase. Therefore, it is preferred to ensure that potentially released small RNA is re-bound to the nucleic acid binding solid phase to ensure a high recovery of small RNA. Depending on the type of nucleic acid binding solid phase used, e.g. whether a column based or particle based approach is used, different procedures are feasible. If particles such as magnetic particles are used as nucleic acid binding solid phase, after performing the optional DNase digest, a chaotropic agent and alcohol can be added, thereby establishing binding conditions that allow to rebind small RNA to the particles. For this purpose, a solution can be used which comprises e.g. a chaotropic salt and/or alcohol. A respective solution may also serve as washing solution. Additional alcohol can also be added separately, in order to increase the alcohol concentration for re-binding. Suitable alcohols, alcohol concentrations, chaotropic salts and chaotropic concentrations were described above in conjunction with step c). The same conditions can be used for rebinding. If a column based nucleic acid binding solid phase is used it is preferred to perform the following steps after performing the optional DNase digest while the RNA is bound to the solid phase (often also referred to as on-column DNase digest):

collecting small RNA which might have been released from the nucleic acid binding solid phase during the DNAase digest as flow through;

contacting said flow through which comprises small RNA mixed with a recovery solution with the nucleic acid binding solid phase for rebinding the contained small RNA to said nucleic acid binding solid phase.

To ensure that RNA that might have been partially released during the on-column DNase digest rebinds to the nucleic acid binding solid phase and to collect released small RNA as flow through, it is preferred to pass a recovery solution through the column after the DNase digest was completed. RNA that can rebind under the conditions that are established by the recovery solution is tightly rebound to the nucleic acid binding solid phase and "escaped" small RNA can be collected as flow through and thus can be reapplied and accordingly can be rebound to the nucleic acid solid phase. This prevents that small RNA gets lost even if an on-column DNase digest is performed. Details of a respective rebinding step following an on column DNase digest are described in WO 2012/028737, herein incorporated by reference. After rebinding potentially escaped small RNA to the nucleic acid binding solid phase, again one or more washing steps can be performed. Suitable conditions were described above.

In case it is desired to perform an elution step to elute the bound nucleic acids from the solid phase, elution can be achieved for example with classical elution solutions such as water, elution buffers, in particular low salt elution buffers. The elution buffers may comprise a biological buffer such as Tris, MOPS, HEPES, MES, BIS-TRIS propane and others. A respective elution step may be performed in step dd). Preferably, elution solutions are used that do not interfere with the intended downstream applications. After elution, the eluate can be heat denatured. However, it is also within the scope of the present invention to release and thus elute the nucleic acids from the solid phase by other or assisting elution means such as e.g. heating.

Subsequently, suitable embodiments are described which allow to isolate total RNA including small RNA from a sample comprising RNA and DNA. Here, embodiments are described which allow to isolate total RNA, including small RNA, or which allow to isolate small RNA as separate fraction from larger RNA and/or in parallel with DNA. Thus, RNA as well as DNA can be isolated from the protein-depleted supernatant that is provided according to the method of the present invention. However, if desired, DNA can be selectively depleted during the purification process thereby providing isolated RNA which is substantially free of DNA, in particular free of genomic DNA. Here, different options exist to remove the DNA. Non-limiting embodiments will be described subsequently.

According to one embodiment, the supernatant obtained in step b) comprises RNA as well as DNA, and RNA and DNA are isolated in step c) by binding both types of nucleic acids to a nucleic acid binding solid phase. RNA and DNA may be eluted in form of total nucleic acids. According to one embodiment, which is feasible if RNA and DNA are both bound to the nucleic acid binding solid phase, a differential elution process can be followed thereby allowing to separately isolate DNA from total RNA, which includes large and small RNA. E.g. the DNA can be selectively eluted prior to eluting the bound RNA or vice versa. Respective differential elution conditions are e.g. described in WO 95/21849 or EP 1 693 453.

According to one embodiment, DNA is removed by selectively binding DNA under appropriate conditions to a nucleic acid solid phase and then separating the DNA bound to the nucleic acid binding solid phase from the remaining supernatant which still comprises the small and large RNA. This can be achieved e.g. by contacting the supernatant with a suitable nucleic acid binding solid phase under conditions wherein mainly DNA but not RNA is bound to the solid phase. Suitable nucleic acid binding solid phases which allow binding of DNA are well-known in the prior art and are also desired therein. In general, the nucleic acid binding solid phases described herein for the RNA binding step, in particular the silicon containing solid phases, can also be used for DNA binding. Suitable methods for selectively binding and thus removing DNA are for example described in EP 0 880 537 and WO 95/21849, herein incorporated by reference. E.g. if lysing the sample using chaotropic agents such as chaotropic salts, binding conditions can be established in the absence of short chained alcohols such as ethanol or isopropanol that are selective for DNA. If desired, the bound DNA may be further used, e.g. further processed and can e.g. optionally be washed and eluted from the nucleic acid binding solid phase thereby providing a DNA fraction which is substantially free of RNA. The respective DNA fraction is then available for analysis. Thus, the present invention also provides a method wherein RNA and DNA may be isolated from the same sample, because in contrast to prior art methods, a protein-depleted supernatant can be provided which comprises besides small and large RNA also DNA, such as genomic DNA. However, if DNA is not of interest, the bound DNA may also be simply discarded if intending to isolate (only) RNA, e.g. small and large RNA either in separate fractions or in form of total RNA, what is preferred. Also in this case such a DNA binding and removal step is favourable, as it reduces the amount of DNA contaminations in the purified RNA.

When binding DNA to a nucleic acid binding solid phase, such as e.g. a silica containing solid phase, and separating the bound DNA from the remaining sample, a DNA depleted RNA containing supernatant is provided from which small RNA as well as large RNA and RNA of intermediate size can be isolated.

In order to further reduce the amount of DNA in the isolated RNA, an intermediate step for degrading DNA using a suitable enzyme can be performed after DNA was removed from the protein-depleted supernatant by binding the DNA to a nucleic acid solid phase as described above. Performing a DNase digest allow to remove remaining traces of DNA. A DNase treatment may be performed after the RNA was bound to the nucleic acid binding solid phase, e.g. as on column DNase digest. Details were described above. Furthermore, a DNase digest may also be performed on the obtained RNA containing eluate.

Furthermore, it is within the scope of the present invention to isolate large RNA and small RNA in form of separate fractions. This can be achieved e.g. by binding RNA having a length >200 nt in a first step to a first nucleic acid binding solid phase using conditions that are selective for such larger RNA species. Thereby, the predominant portion of such larger RNA is bound to the solid phase, while the remaining supernatant comprises small RNA. In a second binding step, small RNA having a length of 200 nt or less is then isolated from the remaining supernatant from which the large RNA was removed. Respective selective binding conditions are well known in the prior art and therefore, do not need to be described in detail. They are also described in the background. Usually, for selectively binding large RNA in the first binding step, an alcohol concentration of less than 40% is used in the binding mixture, e.g. in a concentration that lies in the range of 10% to 37%, 15% to 35% or 20% to 30%, preferably in the presence of a chaotropic salt. After separating the large RNA that was bound to the solid phase, the supernatant remainder still comprises small RNA. The small RNA may then be isolated in a second binding step, e.g. by increasing the alcohol concentration to ≥40%, preferably ≥45%, more preferably ≥50% and binding the small RNA to a nucleic acid binding solid phase. The bound RNA may be washed and eluted. Furthermore, total RNA may be bound to the same solid phase and small RNA can be obtained as enriched fraction separate from larger RNA following e.g. a differential elution protocol. However, it is preferred to isolate total RNA which comprises small RNA having a length of less than 200 nt as well as larger RNA species because such a procedure is very convenient for the user and flexible with respect to the downstream applications of the isolated RNA, because RNA of all sizes (small, intermediate and large) are recovered.

Also other RNA isolation methods can be used in order to isolate RNA from the protein depleted supernatant that is provided using the special precipitation conditions of the invention. RNA isolation methods are e.g. also described in EP 2 163 622 and WO 2009/070558 and the described binding conditions can be used in order to isolate RNA from the supernatant. Generally, under conditions that are suitable to bind small RNA to a nucleic acid binding solid phase, larger RNA will also bind.

Furthermore, DNA may be isolated from the supernatant. Suitable methods are known to the skilled person and also evident from the present disclosure. According to one embodiment, total nucleic acids are isolated from the supernatant. Here, the isolated nucleic acids comprise small RNA, large RNA, RNA of intermediate size as well as DNA. Suitable binding conditions are known to the skilled person and are also evident from the present disclosure.

The isolated nucleic acids can then be analyzed and/or further processed using suitable assay and/or analytical methods. E.g. RNA such as small, large and/or RNA of intermediate size as well as DNA if isolated from the supernatant can be identified, modified, contacted with at least one enzyme, amplified, reverse transcribed, sequenced, contacted with a probe, be detected (their presence or absence) and/or can be quantified. Respective methods are well-known in the prior art and are commonly applied in the medical, diagnostic and/or prognostic field in order to analyze RNA. Thus, the recovered nucleic acids can be analyzed e.g. to identify the presence, absence or severity of a disease state including but not being limited to a multitude of neoplastic diseases, in particular premalignancies and malignancies such as different forms of tumors or cancers. E.g. the isolated nucleic acids can be analyzed in order to detect diagnostic and/or prognostic markers (e.g., fetal- or tumor-derived extracellular nucleic acids) in many fields of application, including but not limited to non-invasive prenatal genetic testing respectively screening, disease screening, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. Thus, as discussed above, the present method may comprise a further step of nucleic acid analysis and/or processing.

Therefore, according to one embodiment, the isolated nucleic acids, such as in particular the isolated RNA, are analyzed to identify, detect, screen for, monitor or exclude a disease and/or at least one fetal characteristic. The analytical methods will depend on the nucleic acid species of interest. The analysis/further processing of the isolated nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, RNA or DNA sequencing, next generation sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

In particular, the present method can be used for the isolation of RNA for any purpose for which the isolation of RNA is commonly desired. Non-limiting examples include, but are not limited to the isolation of RNA for subsequent cDNA synthesis, cDNA library construction, amplification based methods such as reverse transcription PCR, subtractive hybridization, in vitro translation, SAGE technology, expression analysis, expression array and expression-chip analysis, microarray analysis, RNAse and S1 nuclease protection, RNA northern, dot, and slot blotting, micro injection and furthermore, for sequencing applications. Respective technologies are well-known to the skilled person and thus, do not need further description here. The method of the invention is efficient, flexible and does not require the use of phenolic compounds. According to one embodiment, mRNA is reverse transcribed to cDNA and subsequently detected using polymerase chain reaction.

Specific Embodiments

Non-limiting specific embodiments of the method of the invention will be described in the following.

According to one embodiment, the method comprises the following steps
x) optionally disrupting a sample;
a) adding a precipitation buffer to the sample, which optionally is a disrupted sample, to prepare an acidic precipitation mixture
wherein said precipitation buffer comprises a metal cation precipitant and a buffering agent, has a pH value selected from 3.0 to 4.0, 3.1 to 3.9, 3.2 to 3.9, 3.3 to 3.9, 3.4 to 3.9, 3.5 to 3.9 and 3.5 to 3.8 and does not comprise an organic solvent selected from aprotic polar solvents and protic solvents and wherein the acidic precipitation mixture comprises the metal cation precipitant in a concentration selected from 50 mM to 175 mM, 60 mM to 170 mM, 65 mM to 165 mM, 70 mM to 160 mM, 75 mM to 155 mM, 80 mM to 150 mM, 85 mM to 145 mM and 90 mM to 140 mM and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) optionally comprises:
aa) adding at least one alcohol, preferably isopropanol, to the supernatant to provide a binding mixture which comprises the alcohol, preferably isopropanol, in a concentration of ≥35% (v/v), ≥40% (v/v), ≥45% (v/v) or about 50% (v/v);
bb) binding at least small and large RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

According to one embodiment, the method comprises the following steps
x) optionally disrupting a sample;
a) adding a precipitation buffer to the sample, which optionally is a disrupted sample, to prepare an acidic precipitation mixture
wherein said precipitation buffer comprises a metal cation precipitant and a buffering agent, has a pH value selected from 3.3 to 3.9, 3.4 to 3.9, 3.5 to 3.9 and 3.5 to 3.8 and does not comprise an organic solvent selected from aprotic polar solvents and protic solvents and
wherein the acidic precipitation mixture comprises the metal cation precipitant in a concentration selected from 75 mM to 175 mM, 80 mM to 160 mM, 85 mM to 150 mM and 90 mM to 140 mM
and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding at least one alcohol, preferably isopropanol, to the supernatant to provide a binding mixture which comprises the alcohol, preferably isopropanol, in a concentration of ≥35% (v/v), ≥40% (v/v), ≥45% (v/v) or about 50% (v/v);
bb) binding at least small and large RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

According to one embodiment, the method comprises the following steps
x) optionally disrupting a sample;
a) adding a precipitation buffer to the sample, which optionally is a disrupted sample, to prepare an acidic precipitation mixture
wherein said precipitation buffer comprises a metal cation precipitant selected from $Zn^{2+}$, $Cu^{2+}$ and $Al^{3+}$ in form of a dissolved salt, preferably zinc chloride, and a buffering agent, has a pH value selected from 3.3 to 3.9, 3.4 to 3.9, 3.5 to 3.9 and 3.5 to 3.8 and does not comprise an organic solvent selected from aprotic polar solvents and protic solvents and
wherein the acidic precipitation mixture comprises the metal cation precipitant in a concentration selected from 75 mM to 175 mM, 80 mM to 160 mM, 85 mM to 150 mM and 90 mM to 140 mM
and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding at least one alcohol, preferably isopropanol, to the supernatant to provide a binding mixture which comprises the alcohol, preferably isopropanol, in a concentration of ≥35% (v/v), ≥40% (v/v), ≥45% (v/v) or about 50% (v/v);
bb) binding at least small and large RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

According to one embodiment, the method comprises the following steps
x) optionally disrupting a sample;
a) adding a precipitation buffer to the sample, which optionally is a disrupted sample, to prepare an acidic precipitation mixture
wherein said precipitation buffer comprises $Zn^{2+}$ as metal cation precipitant in form of a dissolved salt, preferably zinc chloride, and a buffering agent, has a pH value selected from 3.3 to 3.9, 3.4 to 3.9, 3.5 to 3.9 and 3.5 to 3.8 and does not comprise an organic solvent selected from aprotic polar solvents and protic solvents and
wherein the acidic precipitation mixture comprises $Zn^{2+}$ in a concentration selected from 80 mM to 175 mM, 85 mM to 160 mM, 90 mM to 150 mM, 95 mM to 145 mM and 100 mM to 140 mM
and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding at least one alcohol, preferably isopropanol, to the supernatant to provide a binding mixture which comprises the alcohol, preferably isopropanol, in a concentration of ≥35% (v/v), ≥40% (v/v), ≥45% (v/v) or about 50% (v/v);
bb) binding at least small and large RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

With respect to the above described embodiments it is noted that prior to step a), a step x) may be performed in which the sample is disrupted. Details and preferred conditions were described above also apply here. However, as is described herein and known from the prior art (see WO2016/009059), sample disruption (if necessary) may also occur at the same time when preparing the precipitation mixture. Thus, according to one embodiment, the sample is disrupted at the same time respectively stage when the precipitation buffer is added in step a). Preferably, a precipitation buffer is added in step a) which comprises a metal cation precipitant in form of a dissolved salt, more preferably zinc chloride. Preferred concentration ranges for the alcohol used to establish the binding conditions in step c) aa) and further characteristics of the binding conditions such as the preferred use of a chaotropic agent, were described above and also apply here.

According to one embodiment, the method comprises the following steps
x) disrupting the biological sample using a chaotropic agent;
a) adding a precipitation buffer to the disrupted sample to prepare an acidic precipitation mixture
wherein said precipitation buffer comprises $Zn^{2+}$ as metal cation precipitant in form of zinc chloride, and a buffering agent, has a pH value selected from 3.3 to 3.9, 3.4 to 3.9, 3.5 to 3.9 and 3.5 to 3.8 and does not comprise an organic solvent selected from aprotic polar solvents and protic solvents and
wherein the acidic precipitation mixture comprises $Zn^{2+}$ in a concentration selected from 80 mM to 175 mM, 85 mM to 160 mM, 90 mM to 150 mM, 95 mM to 145 mM and 100 mM to 140 mM and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding isopropanol to the supernatant to provide a binding mixture which comprises isopropanol in a concentration of ≥35% (v/v), ≥40% (v/v), ≥45% (v/v) or about 50% (v/v);
bb) binding at least small and large RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

Preferably, the isopropanol concentration in the binding mixture is selected from ≥35% (v/v) to ≤70% (v/v), ≥40% (v/v) to ≤65% (v/v), ≥45% (v/v) to ≤60% (v/v) and ≥45% (v/v) to ≤55% (v/v). An isopropanol concentration of about 50% is particularly preferred.

The term "sample" is used herein in a broad sense and is intended to include a variety of sources that contain nucleic acids. The sample may be and preferably is a biological sample but the term also includes other, e.g. artificial samples which comprise RNA. Exemplary samples include, but are not limited to, tissues, including but not limited to, liver, spleen, kidney, lung, intestine, brain, heart, muscle, fat, pancreas, cell cultures, body fluids in general; whole blood; serum; plasma; red blood cells; white blood cells; buffy coat, tumor cells, fetal cells, host and graft cells; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; bone marrow aspirates, cells in suspension, as well as lysates, extracts, or materials obtained from any cells and microorganisms and viruses that may be present on or in a sample and the like. Materials obtained from clinical or forensic settings that contain or are suspected to contain RNA are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. Preferably, the sample is selected from the group consisting of cells, tissue, body fluids such as for example blood, blood products such as buffy coat, plasma and serum, urine, liquor, sputum, stool, CSF and sperm, epithelial swabs, biopsies, bone marrow samples and diverse tissue samples. As described above, the sample is preferably disrupted prior to preparing the precipitation mixture. In one embodiment, the sample is a liquid sample. The method according to the present invention is particularly suitable for isolating RNA from protein-rich samples, such as plasma or serum. As is shown by the examples, the method according to the present invention allows to efficiently isolate small as well as large RNA from respective samples even though no phenol is used during purification and no organic solvent selected from aprotic polar solvents and protic solvents is used during preparation of the precipitation mixture.

The method according to the present invention is also suitable to process blood samples in particular blood samples that were stabilized using for example anticoagulants and samples derived from such blood samples such as plasma or serum. Typical anticoagulants that are used for stabilizing blood samples include but are not limited to EDTA and citrate. The method is also suitable for isolating RNA from samples derived from respective stabilized samples such as from plasma or serum samples. Furthermore, RNA can be isolated from serum samples, including serum samples comprising an activator.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. DNA includes, but is not limited to all types of DNA, e.g. gDNA; circular DNA, plasmid DNA and circulating DNA. RNA includes but is not limited to hnRNA; mRNA; extracellular RNA, noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts). Small RNA or the term small RNA species in particular refers to RNA having a chain length of 200 nt or less, 175 nt or less, 150 nt or less, 125 nt or less, 100 nt or less or 75 nt or less and includes but is not limited to miRNA, siRNA, other short interfering nucleic acids, snoRNAs and the like. Large RNA and similar expression as used herein refer to RNA species which have a length of at least 1000 nt such as at least 1250 nt, at least 1500 nt or even larger. Large RNA in particular includes mRNA. In case the RNA is a double-stranded molecule, the chain length indicated as "nt" refers to "bp". The RNA that can be isolated with the present method may of course also be RNA of intermediate size and is e.g. isolated when isolating total RNA from a sample.

The present method is particularly suitable for isolating extracellular nucleic acids, such as total circulating cell-free RNA and DNA, from various biological samples such as in particular plasma and serum. The term "extracellular nucleic acids" or "extracellular nucleic acid" as used herein, in particular refers to nucleic acids that are not contained in cells. Respective extracellular nucleic acids are also often referred to as cell-free nucleic acids. The term "extracellular nucleic acids" refers e.g. to extracellular RNA as well as to extracellular DNA. Examples of typical extracellular nucleic acids that are found in the cell-free fraction (respectively portion) of biological samples such as e.g. body fluids include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. Extracellular nucleic acids may be comprised inside exosomes or other extracellular vesicles. Extracellular nucleic acids can be isolated from the cell-depleted or cell free fraction of biological samples, e.g. derived from a body fluid such as e.g. blood, plasma, serum, saliva, urine, liquor, cerebrospinal fluid, sputum, lachrymal fluid, sweat, amniotic fluid or lymphatic fluid. Cells can be removed from such biological samples using by using known methods such as centrifugation. The extracellular nucleic acids can then be isolated from the obtained cell-free or cell-depleted portion. The isolating of nucleic acids from plasma or serum is particularly preferred. According to one embodiment, the present method comprises a step of analyzing the isolated extracellular nucleic acids.

As nucleic acid binding solid phase that can be used for binding the nucleic acids such as RNA, any material that is capable of binding the nucleic acid of interest can be used. This includes a variety of materials capable of binding nucleic acids. Exemplary solid phases that can be used in conjunction with the present invention include, but are not limited to, compounds comprising silicon, including but not limited to, silica materials such as silica particles, silica fibres, glass fibres, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; minerals, zirconia; alumina; polymeric supports, organic polymers, diethylaminoethyl- and triethylaminoethyl-derivatized supports, hydrophobic chromatography resins and the like. The term solid phase is not intended to imply any limitation regarding its form or design. Thus, the term solid phase encompasses appropriate materials that are porous or non-porous, permeable or impermeable, including but not limited to membranes, filters, sheets, particles, magnetic particles, beads, gels, powders, fibers and the like. According to one embodiment, a solid phase functionalized with anion exchange ligands is used in order to bind the nucleic acid of interest from the protein-depleted supernatant. E.g. a column or particles such as magnetic particles functionalized with anion exchange ligands may be used. According to another embodiment, the surface of the solid phase such as e.g. a silica solid phase is not modified and is, e.g., not modified with functional groups.

Particularly preferred is the use of silicon containing materials such as silica and polysilicic acid materials, borosilicates, silicates and anorganic glasses as solid phase. Here, the solid phase preferably provides a silica surface for interaction with the RNA which may be bound by precipitation and/or adsorption. The term "silica surface" as used herein includes surfaces comprising or consisting of silicon dioxide and/or other silicon oxides, diatomaceous earth, glass, zeolithe, bentonite, alkylsilica, aluminum silicate and borosilicate. The silica surface is preferably unmodified. Therefore, the surface is not modified with nucleic acid binding ligands or other nucleic acid binding groups. E.g., the solid phase does not carry any ligands at its binding surface that comprise ion exchange groups, in particular, the surface of the solid phase is not modified with functional ligands. In particular, it is not modified with ligands comprising anionic or cationic exchange groups such as e.g. amine groups or carboxyl groups. According to one embodiment, the silica surface does not comprise any functional groups besides its silanol groups or other oxidized forms of silicon, like oxides. Exemplary solid phases that can be used in conjunction with the present invention include, but are not limited to, solid phases comprising a silica surface, including but not limited to, silica particles, silica fibres, glass materials such as e.g. glass powder, glass fibres, glass particles or controlled pore glass, silicon dioxide, glass or silica in particulate form such as powder, beads or frits. According to the present invention, the use of a column based solid phase or the use of particles, in particular magnetic particles, is preferred.

Silica based nucleic acid isolation methods are broadly used in the prior art and work particularly well when isolating RNA, including small RNA using a high alcohol concentrations for binding, preferably in combination with at least one chaotropic salt.

According to one embodiment, silica particles are used that may have the form of beads. Preferably, said particles have a size of about 0.02 to 30 μm, more preferred 0.05 to 15 μm and most preferred of 0.1 to 10 μm. To ease the processing of the nucleic acid binding solid phase, preferably magnetic silica particles are used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. The use of magnetic particles is convenient, because the magnetic particles including the bound RNA can be processed easily by the aid of a magnetic field, e.g. by using a permanent magnet. This embodiment is compatible with established robotic systems capable of processing magnetic particles. Here, different robotic systems exist in the prior art that can be used in conjunction with the present invention to process the magnetic particles to which nucleic acids were bound. According to one embodiment, magnetic particles are collected at the bottom or the side of a reaction vessel and the remaining liquid sample is removed from the reaction vessel, leaving behind the collected magnetic particles to which the nucleic acids are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. As respective systems are well-known in the prior art and are also commercially available (e.g. QIASYMPHONY®; QIAGEN), they do not need any detailed description here. In a further alternative system that is known for processing magnetic particles, the sample comprising the magnetic particles can be aspirated into a pipette tip and the magnetic particles can be collected in the pipette tip by applying a magnet e.g. to the side of the pipette tip. The remaining sample can then be released from the pipette tip while the collected magnet particles which carry the bound nucleic acids remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

According to a preferred embodiment, a column based nucleic acid isolation procedure is performed, wherein the solid phase is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the solid phase that is used for RNA binding. Said solid phase comprised in the column should allow the passage of a solution, respectively the binding mixture when applied to the column. This means that if e.g. a centrifuge force is applied to the column, a solution and/or the binding mixture is enabled to pass through the column in direction of the centrifuge force. As discussed above, when using a respective column based isolation procedure, the binding mixture is usually passed through the column, e.g. assisted by centrifugation or vacuum, and the nucleic acid molecules bind to the comprised solid phase during said passage. Which nucleic acid species (e.g. small and/or large RNA) is bound depends on the used binding conditions. The column can be used in a single format or in a multi-format. Such multi-columns having a similar format as multi-well plates and which comprise a solid phase such as a silica membrane or glass fibres, are well-known in the prior art and are also commercially available. Preferably, the column is a spin column. Preferably, a nucleic acid binding membrane or nucleic acid binding fibres are used as solid phase. Examples include but are not limited to silica membranes, glass fibre membranes or filters providing a silicon containing surface for nucleic acid binding. Preferably, the nucleic acid binding solid phase is porous. As is shown by the examples, using a solid phase comprised in a column has several advantages. The use of columns such as spin columns is widely established for RNA purification, and thus, the use of columns is very convenient for the user. Column based methods are also fast and, furthermore, automated systems exist that allow the automated processing of the samples (see e.g. QIAcube, QIAGEN). Thereby, tedious manual handling procedures can be avoided. Furthermore, using a spin column based approach for isolating nucleic acids has the advantage that there is no risk of carryover of potentially inhibitory components from the washing solutions (such as e.g. alcohol) or beads. It is preferred to use a membrane or fibres as solid phase which comprise or consist of silica in the column. Suitable and preferred silica based materials which provide a silica surface suitable for nucleic acid and in particular RNA binding were also described above. A further common solid phase comprised in a column is a fill of silica particles, or a layer of a silica material (e.g. a silica gel). E.g. the silica particles can be arranged as a layer on an inert filter or membrane, thereby forming a nucleic acid binding solid phase. To alleviate the passage of the binding mixture through the solid phase comprised in the column, suitable means can be used such as e.g. centrifugation or the use of a pressure difference-generating apparatus which e.g. presses the sample through the column, respectively the solid phase or sucks it through the solid phase by applying a vacuum. Respective means are well known in the prior art and thus need no further description here.

The above described nucleic acid binding solid phases are generally also suitable for binding DNA as is well-known to the skilled person.

B. Precipitation Buffer

According to a second aspect, a precipitation buffer for precipitating proteins is provided comprising at least one metal cation precipitant and at least one buffering agent, wherein the precipitation buffer has a pH value of 4 or less and wherein the precipitation buffer does not comprise an organic solvent selected from aprotic polar solvents and protic solvents.

The respective precipitation buffer can be advantageously used in order to precipitate proteins from various biological samples, in particular disrupted biological samples. Therefore, it may be specifically used in the methods according to the first aspect of the present invention in order to precipitate proteins. The present invention therefore also pertains to the use of the precipitation buffer according to the second aspect in the method according to the first aspect.

Details of said precipitation buffer were already described above in conjunction with the method according to the first aspect and it is referred to the respective disclosure which also applies here. Non-limiting embodiments are again described briefly in the following.

The metal cation precipitant may be comprised in the precipitation buffer in form of a dissolved salt in a concentration selected from 250 mM to 3M, 500 mM to 2.8M, 0.75M to 2.7 M, 1M to 2.6M, 1.2M to 2.5M, 1.3M to 2.25M and 1.6M to 2M. E.g. halogenide salts such as chloride salts may be used. In case two or more metal cation precipitants are comprised, these concentrations refer according to one embodiment to the overall concentration of the comprised metal cation precipitants. As is demonstrated by the examples, using a precipitation buffer that comprises the metal cation precipitant in a respective concentration provides good results. Suitable metal cation precipitants were already described above, and the respective disclosure also applies here. Preferably, the metal cation precipitant is selected from $Zn^{2+}$, $Cu^{2+}$ and $Al^{3+}$ $Zn^{2+}$ is particularly preferred. It can be comprised in the precipitation buffer as zinc chloride.

The precipitation buffer does not comprise an organic solvent selected from aprotic polar solvents and protic solvents. Such solvents are used in WO2016/009059. The therein described organic solvents are not comprised in the precipitation buffer of the present invention. The present invention allows to avoid all organic solvents in the precipitation mixture.

The precipitation buffer may have a pH value that is selected 2.5 to 4, 2.75 to 4.0, 2.8 to 4.0, 3.0 to 3.9, 3.1 to 3.9, 3.2 to 3.9, 3.3 to 3.9, 3.4 to 3.9 and 3.5 to 3.9. Also, pH values selected from 3.3 to 3.8, 3.4 to 3.8 and 3.5 to 3.8 can be used and are preferred. As is demonstrated by the examples, using an according acidic precipitation buffer is advantageous, in particular when processing protein rich samples such as plasma or serum. The precipitation buffer is preferably suitable to establish and/or maintain a corresponding pH value in the precipitation mixture.

To maintain the acidic pH value, the precipitation buffer comprises at least one buffering agent. Different buffering agents may be used. Also combinations of buffering agents may be used. According to one embodiment, the buffering agent is or is derived from a carboxylic acid. Carboxylic acids include mono-, di- or tri carboxylic acids. Preferably, the buffering agent is acetic acid or citric acid, respectively is an acetate or citrate. As is demonstrated by the examples, acetate and citrate can be added in form of different salts. According to one embodiment, the precipitation buffer comprises the buffering agent in a concentration selected from 300 mM to 3M, 600 mM to 2.75M, 900 mM to 2.5M, 1.2M to 2.4M, 1.4M to 2.3M and 1.5M to 2.25M. Particularly preferred are carboxylic acid salts such as acetate or citrate salts, e.g. alkali metal salts which may be used in the before mentioned concentration ranges. Particularly preferred is a concentration that lies in the range of 1.6 mM to 2.5M, 1.8M to 2.3M or 1.9M to 2.2M. In case two or more buffering agents are used or if the buffing agent is added to the buffer in two or more different forms, such as sodium acetate and acetic acid, the respective concentrations refer according to one embodiment to the overall concentration of the buffering agent in the precipitation buffer.

According to one embodiment, the precipitation buffer
aa) comprises $Zn^{2+}$, $Cu^{2+}$ or $Al^{3+}$, preferably $Zn^{2+}$, as metal cation precipitant in form of a dissolved salt in a concentration selected from 250 mM to 3M, 500 mM to 2.8M, 0.75M to 2.7 M, 1M to 2.6M, 1.2M to 2.5M, 1.3M to 2.25M and 1.6M to 2M; and
bb) has a pH value that lies in a range selected from 3.3 to 3.9, 3.4 to 3.9, 3.5 to 3.9 and 3.5 to 3.8.

As described above $Zn^{2+}$ is preferred and can be comprised e.g. as zinc chloride.

The precipitation buffer according to the third aspect may also be included in a kit. Therefore, the present disclosure also provides a kit. The kit is for isolating a nucleic acid, preferably at least RNA, from a sample. The kit comprises according to one embodiment all reagents that are necessary for isolating the nucleic acid which preferably is at least RNA. According to one embodiment, such kit comprises the precipitation buffer according to the third aspect and one or more of the following components:
- at least one disruption reagent, preferably comprising a chaotropic agent;
- at least one nucleic acid binding solid phase;
- at least one binding solution;
- at least one washing solution; and/or
- at least one elution solution.

The kit comprises according to one embodiment the precipitation buffer, a disruption reagent comprising a chaotropic salt and a nucleic acid binding solid phase. Suitable embodiments for respective disruption reagents and nucleic acid binding solid phases were described above in conjunction with the method according to the first aspect and it is referred to the above disclosure which also applies here. The kit may further comprise a binding solution. The binding solution may comprise or consist of an alcohol suitable to promote binding of a nucleic acid such as preferably RNA to a nucleic acid binding solid phase. Suitable alcohols were described above, preferred are ethanol and isopropanol. This embodiment is e.g. suitable if a silicon containing material is used as nucleic acid binding solid phase. The binding solution may comprise a chaotropic agent such as preferably a chaotropic salt. This is particularly advantageous is case the disruption buffer does not comprise a chaotropic salt.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Thus, for example, reference to "a metal cation precipitant" includes a single type of metal cation precipitant, as well as two or more metal cation precipitants. Likewise, reference to an "alcohol", an "organic solvent", a "chaotropic salt", a "buffering agent" and the like includes single entities and combinations of two or more of such entities. Reference to "the disclosure" and "the invention" and the like includes single or multiple aspects taught herein; and so forth. Aspects taught herein are encompassed by the term "invention".

The term "solution" as used herein in particular refers to a liquid composition, preferably an aqueous composition. It may be a homogenous mixture of only one phase but it is also within the scope of the present invention that a solution comprises solid constituents such as e.g. precipitates.

The term "mixture" as used herein, in particular when used in conjunction with the "precipitation mixture", refers to a composition that may comprise solid constituents such as in particular precipitates unless the context indicates otherwise. As will be appreciated by the skilled reader, when the precipitation buffer is added to the sample to prepare the precipitation mixture, proteins quickly precipitate. Therefore, the precipitation mixture usually is not a mixture of homogenous nature but instead comprises precipitated components.

According to one embodiment, subject matter described herein as comprising certain steps in the case of methods or as comprising certain ingredients in the case of compositions, mixtures, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

FIGURE LEGENDS

FIG. 1 shows the amount of isolated actin mRNA using a precipitation buffer with $ZnCl_2$ and without an organic solvent at different pH values. The pH was adjusted upwards using NaOH (+NaOH) or downwards using acetic acid (+HOAc). The amount of isolated mRNA is displayed by the Ct value, where a higher Ct value indicates a lower amount of RNA.

Figure 2:
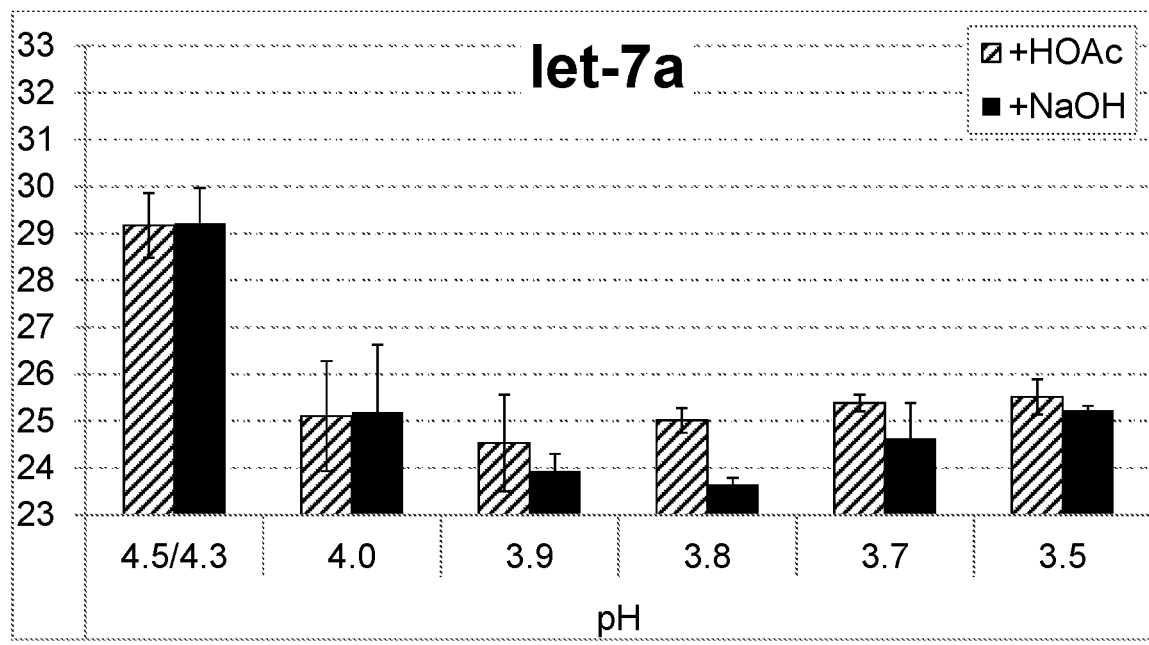

FIG. 2 shows the amount of isolated let-7a miRNA using a precipitation buffer with $ZnCl_2$ and without an organic solvent at different pH values. The pH was adjusted upwards using NaOH (+NaOH) or downwards using acetic acid (+HOAc). The amount of isolated miRNA is displayed by the Ct value, where a higher Ct value indicates a lower amount of RNA.

Figure 3:
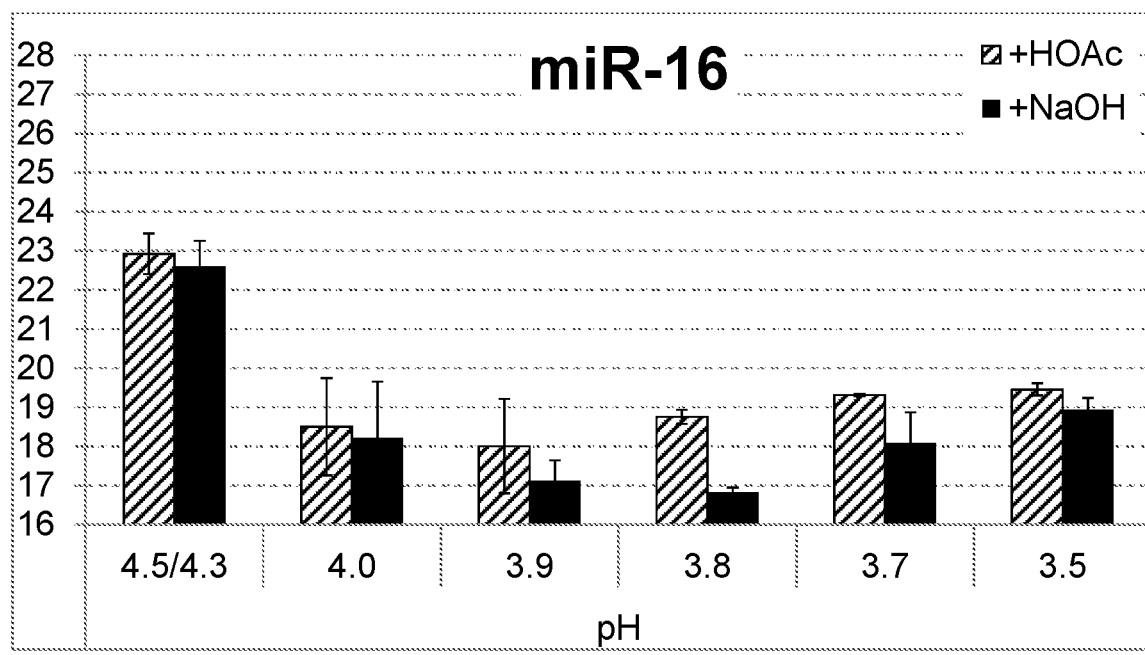

FIG. 3 shows the amount of isolated miR-16 miRNA using a precipitation buffer with $ZnCl_2$ and without an organic solvent at different pH values. The pH was adjusted upwards using NaOH (+NaOH) or downwards using acetic acid (+HOAc). The amount of isolated miRNA is displayed by the Ct value, where a higher Ct value indicates a lower amount of RNA.

Figure 4:
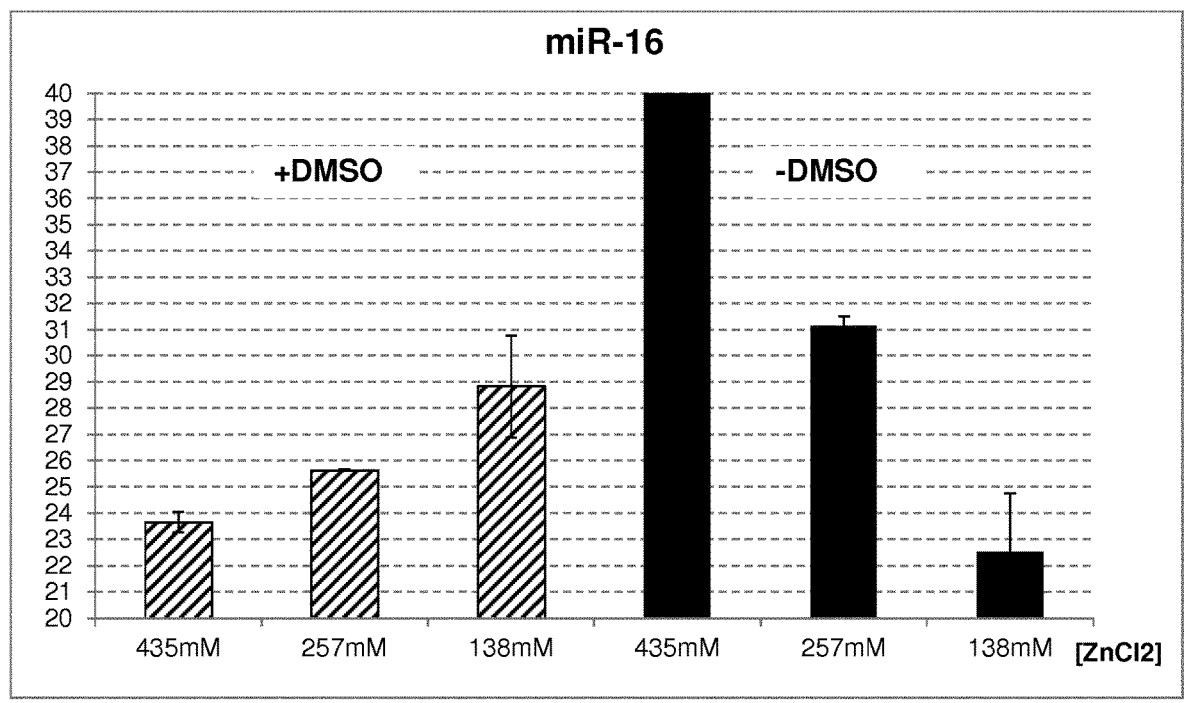

FIG. 4 shows the amount of isolated miR-16 miRNA using different $ZnCl_2$ concentrations with and without an organic solvent for protein precipitation. 435 mM, 257 mM or 138 mM ZnCL2 were used either with or without DMSO. The amount of isolated miRNA is displayed by the Ct value, where a higher Ct value indicates a lower amount of RNA.

EXAMPLES

I. Example 1

1. Materials

Precipitation buffer A: (0% DMSO; $ZnCl_2$ (1.909 M); NaOAc; acidic pH)

Precipitation buffer B: (45% (v/v) DMSO; $ZnCl_2$ (1.909 M); NaOAc; pH 4.0-4.5). This buffer corresponds to Precipitation buffer XP of WO2016/009059.

Silica columns (RNeasy® MinElute® spin columns)

Collection tubes (1.5 ml and 2 ml)

Washing buffer RWT (QIAGEN; contains GTC, 2 volumes ethanol (96%-100%) are added to the buffer concentrate RWT prior to use)

Washing buffer RPE (QIAGEN; 4 volumes ethanol (96%-100%) are added to the buffer concentrate RPE prior to use)

A lysis buffer comprising guanidine thiocyanate.

RNase-free water miScript® primer assay

2. Method

Each condition was tested in triplicate.

Sample Preparation 1 ml pooled plasma is contacted with 300 µl lysis buffer and 24 µl of a non-ionic detergent to disrupt the sample. Sample disruption is supported by vortexing and incubation for 3 min at room temperature.

Protein Precipitation

Approx. 100 µl Precipitation buffer A or B is added to the disrupted sample and vortexed for 20 seconds. This provides a precipitation mixture comprising approx. 140 mM $ZnCl_2$. The sample is then incubated 3 min on ice. Optionally, the samples may also be stored for several hours at 4° C. The obtained precipitate is removed by centrifugation at >12.000×g/4° C. for 10 min.

The nucleic acid containing protein-depleted supernatant is transferred to a new collection tube.

RNA Binding

Alcohol (either ethanol or isopropanol) is added to each supernatant prepared using precipitation buffer A or B to provide the following concentrations in the binding mixture:
35% ethanol
50% isopropanol
55% isopropanol The binding mixture is mixed by pipetting up and down. The binding mixture is then applied to the silica spin column and incubated at room temperature. Afterwards, the columns are centrifuged for 15 seconds at 8.000×g.

Washing Steps

To further purify the bound RNA, several washing steps were performed: 700 µl RWT, centrifugation for 15 seconds at 8000×g, discard flow through; 500 µl RPE, centrifugation for 15 seconds at 8000×g, discard flow through; finally, 500 µl RPE (or 80% ethanol) is added to the column and centrifuged for 2 min at 8000×g; the flow through is discarded.

The column with the washed RNA is then transferred to a new 2 ml collection tube. The column with opened lid is then centrifuged for 5 min at maximum rpm to remove remaining traces of wash solutions.

Elution

The column is transferred to a new 1.5 ml reaction vessel. 30 µl RNase-free water is applied to the middle of the column. The column is closed incubated for 1 min at RT. It is then centrifuged for 1 min at maximum rpm.

3. Analysis

Analysis of Large RNA (Actin)

After cDNA synthesis, a beta-actin qPCR was performed. The mean Ct results of the assay are shown in the below table:

TABLE 1

| Alcohol | Precipitation buffer | Mean Ct actin | Standard deviation |
|---|---|---|---|
| 35% (v/v) ethanol | A | 30.345 | 2.55 |
| | B | 33.496 | 0.82 |
| 50% (v/v) isopropanol | A | 29,464 | 0.36 |
| | B | 36.323 | 1.24 |
| 55% (v/v) isopropanol | A | 28.423 | 0.49 |
| | B | 33.655 | 0.58 |

Analysis of Small RNA

5 µl of each eluate was subsequently used for cDNA synthesis and analysis using the miScript miRNA PCR array. The mean Ct results for let-7a and miR-16 assays are shown in the below table:

TABLE 2

| Alcohol | Precipitation buffer | Mean Ct let-7a | Standard deviation | Mean Ct miR-16 | Standard deviation |
|---|---|---|---|---|---|
| 35% (v/v) ethanol | A | 25.469 | 1.46 | 18.609 | 1.87 |
| | B | 30.821 | 0.51 | 25.014 | 0.17 |
| 50% (v/v) isopropanol | A | 25.399 | 0.44 | 18.188 | 0.53 |
| | B | 30.712 | 0.12 | 25.303 | 0.06 |
| 55% (v/v) isopropanol | A | 24.,651 | 0.04 | 18.312 | 0.09 |
| | B | 28.549 | 0.14 | 24.480 | 0.21 |

Summary

As can be seen, when using the conditions of the present invention, an organic solvent such as DMSO in the precipitation mixture is not required to prevent co-precipitation of long RNA (such as mRNA) together with proteins. The present method achieved better results (i.e. lower Ct values). Best mRNA recovery was observed under the used conditions that used a low concentration of zinc chloride in the precipitation mixture (less than 200 mM—here approx. 140 mM) in the absence of the organic solvent, using different alcohol types and concentrations for RNA binding. mRNA recovery was particularly good using 50-55% isopropanol for nucleic acid binding. The used conditions also allowed the recovery of small RNA (miRNA) and DNA.

Small and large RNA and accordingly, miRNA as well as mRNA, can be efficiently isolated using the method of the invention. Furthermore, the method allowed the isolation of DNA (tested based on 18SDNA) with similar or better results under the above conditions.

II. Example 2

To test the influence of the pH of the precipitation buffer on RNA isolation, precipitation buffer with varying pH was used. The methods as described in example 1 were used for isolation of mRNA or small RNA. The pH of precipitation buffer A was adjusted to a 3.5, 3.7, 3.8, 3.9, 4.0 and 4.3/4.5 as control. Each pH adjustment was done twice, once the pH was adjusted upwards using NaOH and once the pH was adjusted downwards using acetic acid. Thereby, it was ensured that the observed effect is only based on the pH value. Isolation of the mRNA of actin or the small RNA let-7a or miR-16 was analyzed. All steps were performed as described in example 1.

The mean Ct results of the RNA isolation dependent on the pH of the precipitation buffer are shown in FIGS. 1 to 3. As demonstrated, better results (lower Ct values) are obtained using a precipitation buffer with a pH of 4.0 or lower. Using a pH of 4.3 or 4.5, much higher Ct values are observed, indicating a much lower amount of isolated RNA. These results are obtained for large RNA as well as small RNA.

Small and large RNA and accordingly, miRNA as well as mRNA, can be efficiently isolated using the method of the invention, in particular using a precipitation buffer with a pH of 4.0 or lower.

III. Example 3

1. Materials

Precipitation buffer A: (0% DMSO; $ZnCl_2$ (1.909 M); NaOAc; acidic pH)

Precipitation buffer B: (45% (v/v) DMSO; $ZnCl_2$ (1.909 M); NaOAc; pH 4.0-4.5). This buffer corresponds to Precipitation buffer XP of WO2016/009059.

Silica columns (RNeasy® MinElute® spin columns)
Collection tubes (1.5 ml and 2 ml)
Washing buffer RWT (QIAGEN; contains GTC, 2 volumes ethanol (96%-100%) are added to the buffer concentrate RWT prior to use)
Washing buffer RPE (QIAGEN; 4 volumes ethanol (96%-100%) are added to the buffer concentrate RPE prior to use)
A lysis buffer comprising guanidine thiocyanate.
RNase-free water
miScript® primer assay 2. Method Each condition was tested in triplicate.

Sample Preparation

200 µl pooled plasma is contacted with 120 µl lysis buffer to disrupt the sample. Sample disruption is supported by vortexing and incubation for 3 min at room temperature.

Protein Precipitation

95 µl, 50 µl or 25 µl of precipitation buffer A or B is added to the disrupted sample and vortexed for 3 seconds. This provides a precipitation mixture comprising 435 mM, 257 nM or 138 mM $ZnCl_2$, respectively. The sample is then incubated 3 min on ice. The obtained precipitate is removed by centrifugation at >12.000×g/4° C. for 10 min. The nucleic acid containing protein-depleted supernatant is transferred to a new collection tube.

RNA Binding 1 volume isopropanol is added to each supernatant prepared using precipitation buffer A or B. The binding mixture is mixed by pipetting up and down and is then applied to the silica spin column and incubated at room temperature. Afterwards, the columns are centrifuged for 15 seconds at 8.000×g.

Washing Steps

To further purify the bound RNA, several washing steps were performed: 700 µl RWT, centrifugation for 15 seconds at 8200×g, discard flow through; 500 µl RPE, centrifugation for 15 seconds at 8200×g, discard flow through; finally, 500 µl 80% ethanol is added to the column and centrifuged for 2 min at 8200×g; the flow through is discarded. The column with the washed RNA is then transferred to a new 2 ml collection tube. The column with opened lid is then centrifuged for 5 min at maximum rpm to remove remaining traces of wash solutions.

Elution

The column is transferred to a new 1.5 ml reaction vessel. 20 µl RNase-free water is applied to the middle of the column. The column is closed incubated for 1 min at RT. It is then centrifuged for 1 min at maximum rpm.

3. Analysis

Analysis of Small RNA

4 µl of each eluate was subsequently used for cDNA synthesis and analysis using the miScript miRNA PCR array. The mean Ct results for a miR-16 assay dependent on the amount of ZnCL2 and the presence of DMSO are shown in FIG. 4.

Summary

As can be seen, when using the conditions of the present invention, i.e. a precipitation buffer without an organic solvent such as DMSO, a lower concentration of $ZnCl_2$ in the precipitation mixture provides markedly higher amounts of isolated miRNA (indicated by lower Ct values). Best miRNA recovery was observed under the used conditions that used a low concentration of zinc chloride in the precipitation mixture (less than 200 mM—here approx. 140 mM) in the absence of the organic solvent. Similar results were obtained with other miRNAs and mRNA.

Thus, small and large RNA and accordingly, miRNA as well as mRNA, can be efficiently isolated using the method of the invention.

The invention claimed is:

1. A phenol-free method for isolating a nucleic acid from a sample, said method comprising the following steps:
   a) adding a precipitation buffer to a sample to prepare an acidic precipitation mixture wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM and precipitating proteins;
   b) separating the precipitate from the supernatant, wherein the supernatant comprises small RNA having a length of less than 200 nt and large RNA having a length of at least 1000 nt; and
   c) isolating a nucleic acid from the supernatant.

2. The method according to claim 1, wherein the metal cation precipitant is selected from $Zn^{2+}$, $Cu^{2+}$ and $Al^{3+}$.

3. The method according to claim 1, having one or more of the following characteristics:
   i) the precipitation mixture provided in step a) comprises the metal cation precipitant in a concentration of 175 mM or less, 170 mM or less, 165 mM or less, 160 mM or less, 155 mM or less, 150 mM or less, 145 mM or less or 140 mM or less;
   ii) the precipitation mixture provided in step a) comprises the metal cation precipitant in a concentration of at least 50 mM, at least 60 mM, at least 65 mM, at least 70 mM, at least 75 mM, at least 80 mM, at least 85 mM, at least 90 mM, at least 95 mM or at least 100 mM;
   iii) the precipitation mixture provided in step a) comprises the metal cation precipitant in a concentration selected from 50 mM to 175 mM, 60 mM to 170 mM, 65 mM to 165 mM, 70 mM to 160 mM, 75 mM to 155 mM, 80 mM to 150 mM, 85 mM to 145 mM and 90 mM to 140 mM; and/or
   iv) the precipitation buffer comprises a dissolved salt of the metal cation precipitant.

4. The method according to claim 1, wherein the precipitation buffer comprises the metal cation precipitant in a concentration selected from 250 mM to 3M, 500 mM to 2.8 M, 0.75 M to 2.7 M, 1M to 2.6 M, 1.25 M to 2.5 M, 1.5 M to 2.25 M, and 1.7M to 2 M.

5. The method according to claim 1, wherein the precipitation buffer is an aqueous solution that has a pH value selected from 2.5 to 4, 2.75 to 4.0, 2.8 to 4.0, 3.0 to 4.0, 3.1 to 3.9, 3.2 to 3.9, 3.3 to 3.9, 3.4 to 3.9, 3.5 to 3.9, and 3.5 to 3.8.

6. The method according to claim 1, wherein the precipitation buffer is an aqueous solution that
   (i) comprises the metal cation precipitant in a concentration in the range of from 1M to 3M and has a pH value in the range of from 3.0 to 4.0, or
   (ii) comprises the metal cation precipitant in a concentration in the range of from 1.25M to 2.5M and has a pH value in the range of from 3.3 to 3.9, or
   (iii) comprises the metal cation precipitant in a concentration in the range of from 1.5M to 2.25M and has a pH value in the range of from 3.4 to 3.9, or
   (iv) comprises the metal cation precipitant in a concentration in the range of from 1M to 3M and has a pH value in the range of from 3.5 to 3.9, or
   (v) comprises the metal cation precipitant in a concentration in the range of from 1.7M to 2.1M and has a pH value in the range of from 3.0 to 4.0, or
   (vi) comprises the metal cation precipitant in a concentration in the range of from 1.7M to 2.1M and has a pH value in the range of from 3.5 to 3.9.

7. The method according to claim 1, wherein the nucleic acid to be isolated is RNA and wherein step c) comprises isolating at least small and/or large RNA from the supernatant.

8. The method according to claim 7, wherein RNA is isolated in step c) using a nucleic acid binding solid phase and wherein at least one alcohol and/or at least one chaotropic salt is used to establish RNA binding conditions.

9. The method according to claim 1, wherein step c) comprises:
   aa) adding at least one alcohol to the supernatant to provide a binding mixture which comprises the alcohol in a concentration of ≥35% (v/v), ≥40% (v/v) or ≥45% (v/v);
   bb) binding at least large and small RNA contained in the binding mixture to a silicon containing nucleic acid binding solid phase, wherein after step bb), at least large and small RNA is bound to the solid phase;
   cc) optionally washing the bound RNA; and
   dd) optionally eluting RNA from the solid phase.

10. The method according to claim 1, wherein step c) comprises adding alcohol to the supernatant to prepare binding conditions.

11. The method according to claim 9, wherein the provided binding mixture comprises ethanol and/or isopropanol in a concentration selected from 35% (v/v) to 70% (v/v), 40% (v/v) to 65% (v/v), 45% (v/v) to 60% (v/v) and 45% (v/v) to 55% (v/v).

12. The method according to claim 1, wherein sample disruption occurs prior to addition of the precipitation buffer and/or at the same time/stage when the precipitation mixture is prepared.

13. The method according to claim 1, wherein the method comprises
   x) disrupting a sample;
   a) adding a precipitation buffer to the disrupted sample to prepare an acidic precipitation mixture
      wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM
      and precipitating proteins;
   b) separating the precipitate from the supernatant, wherein the supernatant comprises small RNA having a length of less than 200 nt and large RNA having a length of at least 1000 nt; and
   c) isolating a nucleic acid from the supernatant.

14. The method according to claim 1, wherein the method comprises
   a) adding a precipitation buffer and at least one disruption reagent to the sample to disrupt the sample and to prepare an acidic precipitation mixture wherein said precipitation buffer comprises a metal cation precipitant and a buffering agent, has a pH value of 4.0 or less and does not comprise an organic solvent selected from aprotic polar solvents and protic solvents and wherein the acidic precipitation mixture comprises the metal cation precipitant in a concentration of less than 200 mM and comprises the disruption reagent and precipitating proteins;
   b) separating the precipitate from the supernatant, wherein the supernatant comprises small RNA having a length of less than 200 nt and large RNA having a length of at least 1000 nt; and
   c) isolating a nucleic acid from the supernatant.

15. The method according to claim 1, having one or more of the following characteristics:
   i) total RNA is isolated from the supernatant;
   ii) small RNA is isolated in form of an enriched fraction;
   iii) at least mRNA is isolated from the supernatant and subsequently detected;
   iv) the supernatant comprising small RNA and large RNA additionally comprises genomic DNA;
   v) total nucleic acids are isolated from the supernatant;
   vi) genomic DNA is isolated separately from RNA from the supernatant;
   vii) extracellular nucleic acids are isolated from a cell-depleted or cell-free biological samples; and/or
   vii) in step c), RNA is bound to a nucleic acid binding solid phase which optionally, is a silicon containing material such as silica, a polysilicic acid material, a borosilicate, a silicate or glass.

16. The method according to claim 1, for isolating nucleic acids comprising or substantially consisting of RNA, wherein the method comprises the following steps
   x) optionally disrupting the sample;
   a) adding a precipitation buffer to the optionally disrupted sample to prepare an acidic precipitation mixture
      wherein said precipitation buffer comprises a metal cation precipitant and a buffering agent, has a pH value selected from 3.0 to 4.0, 3.1 to 3.9, 3.2 to 3.9, 3.3 to 3.9, 3.4 to 3.9, 3.5 to 3.9 and 3.5 to 3.8 and does not comprise an organic solvent selected from aprotic polar solvents and protic solvents and
      wherein the acidic precipitation mixture comprises the metal cation precipitant in a concentration selected from 50 mM to 175 mM, 60 mM to 170 mM, 65 mM to 165 mM, 70 mM to 160 mM, 75 mM to 155 mM, 80 mM to 150 mM, 85 mM to 145 mM and 90 mM to 140 mM and precipitating proteins;
   b) separating the precipitate from the supernatant, wherein the supernatant comprises small RNA having a length of less than 200 nt and large RNA having a length of at least 1000 nt; and
   c) isolating at least small and large RNA from the supernatant, wherein step c) optionally comprises:
      aa) adding at least one alcohol to the supernatant to provide a binding mixture which comprises the alcohol in a concentration of ≥35% (v/v), ≥40% (v/v), ≥45% (v/v) or about 50% (v/v);
      bb) binding nucleic acids contained in the binding mixture to a silicon containing nucleic acid binding solid phase, wherein after step bb), at least large and small RNA is bound to the solid phase;
      cc) optionally washing the bound RNA;
      dd) eluting RNA from the solid phase.

17. The method according to claim 1, wherein the precipitation buffer is added to the sample in a ratio in the range selected from 1:1 to 1:30, 1:5 to 1:20, 1:8 to 1:17, 1:10 to 1:15, and 1:12 to 1:14 (precipitation buffer: sample).

18. A precipitation buffer for precipitating proteins comprising at least one metal cation precipitant and at least one buffering agent, wherein the precipitation buffer has a pH value of 4 or less and wherein the precipitation buffer does not comprise an organic solvent selected from aprotic polar solvents and protic solvents.

19. The precipitation buffer according to claim 18, having one or more of the following characteristics:
   i) the metal cation precipitant is selected from $Zn^{2+}$, $Cu^{2+}$ and $Al^{3+}$;
   ii) the buffering agent is or is derived from a carboxylic acid or phosphate;
   iii) it comprises the metal cation precipitant in a concentration selected from 250 mM to 3M, 500 mM to 2.8M, 0.75M to 2.7 M, 1M to 2.6M, 1.25M to 2.5M, 1.5M to 2.25M and 1.7M to 2M;

iv) it has a pH value that lies in a range selected from 2.5 to 4, 2.75 to 4.0, 2.8 to 4.0, 3.0 to 4.0, 3.1 to 3.9, 3.2 to 3.9, 3.3 to 3.9, 3.4 to 3.9, 3.5 to 3.9 and 3.5 to 3.8;
v) it comprises the buffering agent in a concentration selected from 300 mM to 3M, 600 mM to 2.75M, 900 mM to 2.5M, 1.2M to 2.4M, 1.4M to 2.3M and 1.5M to 2.25M;

and/or vi) the precipitation buffer
   aa) comprises $Zn^{2+}$, $Cu^{2+}$ or $Al^{3+}$, as metal cation precipitant in form of a dissolved salt in a concentration selected from 250 mM to 3M, 500 mM to 2.8M, 0.75M to 2.7 M, 1M to 2.6M, 1.2M to 2.5M, 1.3M to 2.25M and 1.6M to 2M; and
   bb) has a pH value that lies in a range selected from 3.3 to 3.9, 3.4 to 3.9, 3.5 to 3.9 and 3.5 to 3.8.

\* \* \* \* \*